| (12) | United States Patent | (10) Patent No.: US 10,300,260 B2 |
|---|---|---|
| | Wirtanen et al. | (45) Date of Patent: May 28, 2019 |

(54) APPLICATOR AND METHOD FOR APPLYING A MICRONEEDLE DEVICE TO SKIN

(71) Applicant: 3M INNOVATIVE PROPERTIES COMPANY, St. Paul, MN (US)

(72) Inventors: David J. Wirtanen, Stillwater, MN (US); Kevin L. Puckett, Hudson, WI (US); James L. Schug, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 239 days.

(21) Appl. No.: 14/432,500

(22) PCT Filed: Oct. 10, 2013

(86) PCT No.: PCT/US2013/064275
§ 371 (c)(1),
(2) Date: Mar. 31, 2015

(87) PCT Pub. No.: WO2014/059104
PCT Pub. Date: Apr. 17, 2014

(65) Prior Publication Data
US 2015/0290444 A1    Oct. 15, 2015

Related U.S. Application Data

(60) Provisional application No. 61/711,817, filed on Oct. 10, 2012.

(51) Int. Cl.
*A61M 37/00* (2006.01)
*A61B 17/20* (2006.01)

(52) U.S. Cl.
CPC ....... *A61M 37/0015* (2013.01); *A61B 17/205* (2013.01); *A61M 2037/003* (2013.01);
(Continued)

(58) Field of Classification Search
CPC ...... A61M 37/0015; A61M 2037/0023; A61M 2037/003; A61M 2037/0046;
(Continued)

(56) References Cited

U.S. PATENT DOCUMENTS 4,472,480 A    9/1984 Olson
4,584,355 A    4/1986 Blizzard
(Continued)

FOREIGN PATENT DOCUMENTS

WO    2006-055795    5/2006
WO    2006-062848    6/2006
(Continued)

OTHER PUBLICATIONS

International Search Report for PCT International Application No. PCT/US2013/064275, dated Dec. 20, 2013, 4pgs.

*Primary Examiner* — Bradley J Osinski
*Assistant Examiner* — Nilay J Shah
(74) *Attorney, Agent, or Firm* — Eric E. Silverman

(57) ABSTRACT

An applicator and method for applying a microneedle device to skin. The applicator can include a microneedle device and a housing configured to house the microneedle device. The housing can have a first surface configured to be positioned toward the skin. The applicator can include (i) an unactuated state in which the microneedle device is located within the housing and does not extend beyond the first surface of the housing, and (ii) an actuated state in which at least a portion of the microneedle device extends beyond the first surface of the housing. The applicator can further include a locking mechanism configured to lock the applicator in the actuated state. The method can include positioning the first surface of the housing of the applicator adjacent the skin; actuating the applicator to cause the applicator to change to the actuated state; and locking the applicator in the actuated state.

19 Claims, 8 Drawing Sheets

(52) U.S. Cl.
CPC .............. *A61M 2037/0023* (2013.01); *A61M 2037/0046* (2013.01); *A61M 2037/0053* (2013.01); *A61M 2037/0061* (2013.01)

(58) Field of Classification Search
CPC .. A61M 2037/0053; A61M 2037/0061; A61M 2005/14252; A61M 2005/14284; A61M 2005/1585; A61M 5/158; A61M 2005/1426; A61M 5/1626; A61M 5/3243; A61B 17/205
See application file for complete search history.

(56) References Cited

U.S. PATENT DOCUMENTS

| | | | |
|---|---|---|---|
| 4,585,836 A | | 4/1986 | Homan |
| 4,591,622 A | | 5/1986 | Blizzard |
| 4,655,767 A | | 4/1987 | Woodard |
| 4,693,776 A | | 9/1987 | Krampe |
| 4,752,290 A | * | 6/1988 | Schramm ............ A61M 5/3243 604/198 |
| 5,223,261 A | | 6/1993 | Nelson |
| 5,352,216 A | * | 10/1994 | Shiono .............. A61F 13/00034 602/60 |
| 5,380,760 A | | 1/1995 | Wendel |
| 5,656,286 A | | 8/1997 | Miranda |
| 6,091,975 A | | 7/2000 | Daddona |
| 6,312,612 B1 | | 11/2001 | Sherman |
| 6,379,324 B1 | | 4/2002 | Garstein |
| 6,558,361 B1 | | 5/2003 | Yeshurun |
| 6,855,131 B2 | | 2/2005 | Trautman |
| 7,014,625 B2 | * | 3/2006 | Bengtsson ......... A61M 5/14248 604/131 |
| 7,648,484 B2 | | 1/2010 | Yeshurun |
| 2002/0077584 A1 | * | 6/2002 | Lin .................... A61B 5/14532 604/21 |
| 2004/0049150 A1 | | 3/2004 | Dalton |
| 2005/0165358 A1 | | 7/2005 | Yeshurun |
| 2005/0261631 A1 | | 11/2005 | Clarke |
| 2006/0095061 A1 | | 5/2006 | Trautman |
| 2007/0185515 A1 | | 8/2007 | Stout |
| 2008/0108958 A1 | | 5/2008 | Carter |
| 2008/0114298 A1 | | 5/2008 | Cantor |
| 2008/0183144 A1 | * | 7/2008 | Trautman .......... A61M 37/0015 604/272 |
| 2008/0195035 A1 | | 8/2008 | Frederickson |
| 2009/0198189 A1 | | 8/2009 | Simons |
| 2011/0213335 A1 | | 9/2011 | Burton |
| 2011/0276027 A1 | * | 11/2011 | Trautman .......... A61M 37/0015 604/506 |
| 2012/0123387 A1 | | 5/2012 | Gonzalez |

FOREIGN PATENT DOCUMENTS

| | | |
|---|---|---|
| WO | 2007-124411 | 11/2007 |
| WO | 2011/014514 | 2/2011 |
| WO | 2011-115602 | 9/2011 |
| WO | 2012-074576 | 6/2012 |
| WO | 2012-122162 | 9/2012 |
| WO | 2013-055638 | 4/2013 |
| WO | 2013-055641 | 4/2013 |
| WO | 2014/058746 | 4/2014 |

* cited by examiner

APPLICATOR AND METHOD FOR APPLYING A MICRONEEDLE DEVICE TO SKIN

CROSS REFERENCE TO RELATED APPLICATIONS

This is a national stage filing under 35 U.S.C. § 371 of PCT/US2013/064275, filed Oct. 10, 2013, which claims priority to U.S. Provisional Application No. 61/711,817, filed Oct. 10, 2012, the disclosure of which is incorporated herein by reference in its entirety.

FIELD

The present disclosure generally relates to applicators and methods for applying a microneedle device to skin to treat an area of the skin and/or to deliver an active agent to the skin.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells, that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays can be used in conjunction with an applicator device capable of being used several times or as a single-use device. The microneedle arrays are generally used once and then discarded.

Issues related to applying microneedles include the ability to effectively and consistently insert the needles to a desired depth in the skin, the ability to reliably hold the microneedles in proper contact with the skin during the period of administration, and the ability to apply consistent force for delivery.

SUMMARY

The present disclosure relates to applicators that can be used to treat a selected site (e.g., on skin), and/or to apply an active ingredient to the treated site. One feature and advantage of applicators of the present disclosure is that they can be locked in an actuated (e.g., treatment and/or delivery) state where microneedles can be puncturing skin. The applicator can then remain on the skin for a desired treatment and/or delivery period and can be removed from the skin (e.g., as a whole) when desired.

One aspect of the present disclosure provides an applicator for applying a microneedle device to a skin surface. The applicator can include a microneedle device and a housing configured to house at least a portion of the microneedle device. The housing can have a first surface configured to be positioned toward the skin surface. The applicator can include (i) an unactuated state in which the microneedle device is located within the housing and does not extend beyond the first surface of the housing; and (ii) an actuated state in which at least a portion of the microneedle device extends beyond the first surface of the housing. The applicator can further include a locking mechanism configured to lock the applicator in the actuated state.

Another aspect of the present disclosure provides a method of applying a microneedle device to a skin surface. The method can include providing an applicator comprising: a microneedle device; a housing configured to house at least a portion of the microneedle device, the housing having a first surface configured to be positioned toward the skin surface; an unactuated state in which the microneedle device is located within the housing and does not extend beyond the first surface of the housing; and an actuated state in which at least a portion of the microneedle device extends beyond the first surface of the housing. The method can further include positioning the first surface of the housing of the applicator adjacent the skin surface; actuating the applicator to cause the applicator to change to the actuated state; and locking the applicator in the actuated state.

Another aspect of the present disclosure provides an applicator for applying a microneedle device to a skin surface. The applicator can include a housing having a first surface configured to be positioned toward the skin surface. The housing can include a bore that that extends through the first surface and a microneedle device comprising an array of microneedles oriented toward the first surface of the housing. The applicator can further include a plunger dimensioned to be at least partially received in the bore of the housing located adjacent the microneedle device, the plunger being movable relative to the housing between a first position and a second position to move the microneedle device, respectively, between (i) a first position in which the microneedle device is recessed relative to the first surface of the housing, and (ii) a second position in which at least a portion of the microneedle device extends beyond the first surface of the housing. The applicator can further include a locking mechanism configured to lock the microneedle device in the second position.

Another aspect of the present disclosure provides an applicator for applying a microneedle device to a skin surface. The applicator can include a housing having a first surface configured to be positioned toward the skin surface. The housing can include a bore that extends through the first surface and a deformable sheet positioned to extend across the bore of the housing. The deformable sheet can be spaced a distance from the first surface of the housing. The deformable sheet can have a first side oriented toward the first surface of the housing and a second side opposite the first side. The applicator can further include a microneedle device coupled to the first side of the deformable sheet, such that the microneedle device is oriented toward the first surface of the housing, and a plunger dimensioned to be at least partially received in the bore of the housing adjacent the second side of deformable sheet and located opposite the deformable sheet from the microneedle device. The plunger can be movable relative to the housing between a first position and a second position to move the microneedle device, respectively, between (i) a first position in which the microneedle device is recessed relative to the first surface of the housing, and (ii) a second position in which at least a portion of the microneedle device extends beyond the first surface of the housing. The applicator can further include a locking mechanism configured to lock the microneedle device in the second position.

Another aspect of the present disclosure provides a method of applying a microneedle device to a skin surface. The method can include providing an applicator comprising: a housing having a first surface configured to be positioned toward the skin surface, the housing comprising a bore that that extends through the first surface; a microneedle device comprising a microneedle array of microneedles oriented toward the first surface of the housing; and a plunger dimensioned to be at least partially received in the bore of the housing located adjacent the microneedle array. The plunger can be movable relative to the housing between a first position and a second position to move the microneedle device, respectively, between (i) a first position in which the microneedle device is recessed relative to the first surface of the housing, and (ii) a second position in which at least a portion of the microneedle device extends beyond the first surface of the housing. The method can further include positioning the first surface of the housing adjacent the skin surface; moving the plunger from the first position to the second position to move the microneedle device from the first position to the second position; and locking the microneedle device in the second position.

Another aspect of the present disclosure provides a method of applying a microneedle device to a skin surface. The method can include providing an applicator comprising: a housing having a first surface configured to be positioned toward the skin surface, the housing comprising a bore that extends through the first surface; a deformable sheet positioned to extend across the bore of the housing, the deformable sheet having a first side oriented toward the first surface of the housing and a second side opposite the first side; a microneedle device coupled to the first side of the deformable sheet, such that the microneedle device is oriented toward the first surface of the housing; and a plunger dimensioned to be at least partially received in the bore of the housing adjacent the second side of deformable sheet and located opposite the deformable sheet from the microneedle device. The plunger can be movable relative to the housing between a first position and a second position to move the microneedle device, respectively, between (i) a first position in which the microneedle device is recessed relative to the first surface of the housing, and (ii) a second position in which at least a portion of the microneedle device extends beyond the first surface of the housing. The method can further include positioning the first surface of the housing adjacent the skin surface; moving the plunger from the first position to the second position; and locking the microneedle device in the second position.

Another aspect of the present disclosure provides a method for coating a microneedle device with an active agent. The method can include providing an applicator comprising: a housing having a first surface configured to be positioned toward the skin surface, the housing comprising a bore that extends through the first surface; a deformable sheet positioned to extend across the bore of the housing, the deformable sheet having a first side oriented toward the first surface of the housing and a second side opposite the first side; a microneedle device coupled to the first side of the deformable sheet, such that the microneedle device is oriented toward the first surface of the housing; and a plunger dimensioned to be at least partially received in the bore of the housing adjacent the second side of deformable sheet and located opposite the deformable sheet from the microneedle device. The plunger can be movable relative to the housing between a first position, a second position and a third position to move the microneedle device, respectively, between (i) a first position in which the microneedle device is recessed relative to the first surface of the housing, (ii) a second position in which the microneedle device extends beyond the first surface of the housing and a locking mechanism is activated to lock the plunger and the microneedle device in the second position, and (iii) a third position located intermediately of the first position and the second position in which at least a portion of the microneedle device extends beyond the first surface of the housing. The method can further include coating at least a portion of the microneedle device with the active agent by moving the plunger and the microneedle device to the third position; and moving the plunger and the microneedle device from the third position to the first position (or another location at which the microneedle device is located within the housing) to locate the coated microneedle device within the housing.

Another aspect of the present disclosure provides an applicator for applying a microneedle device to a skin surface. The applicator can include a housing having a first surface configured to be positioned toward the skin surface. The housing can include a bore that extends through the first surface. The applicator can further include a deformable sheet positioned to extend across the bore of the housing such that the deformable sheet is spaced a distance from the first surface of the housing. The deformable sheet can have a first side oriented toward the first surface of the housing and a second side opposite the first side. The deformable sheet can also have a first state and a second state. The applicator can further include a microneedle device coupled to the first side of the deformable sheet, such that the microneedle device is oriented toward the first surface of the housing and is located within the housing and recessed relative to the first surface of the housing when the deformable sheet is in the first state. The applicator can further include a plunger dimensioned to be at least partially received in the bore of the housing adjacent the second side of the deformable sheet and located opposite the deformable sheet from the microneedle device. The plunger can be movable relative to the housing between a first position and a second position to move the microneedle device, respectively, between (i) a first position in which the deformable sheet is in its first state, and in which the microneedle device is located within the bore of the housing and recessed relative to the first surface of the housing, and (ii) a second position in which the deformable sheet is in its second state and at least a portion of the microneedle device extends beyond the first surface of the housing. The applicator can further include a locking mechanism configured to lock the microneedle device in the second position.

Other features and aspects of the present disclosure will become apparent by consideration of the detailed description and accompanying drawings.

DETAILED DESCRIPTION

Figure 1:
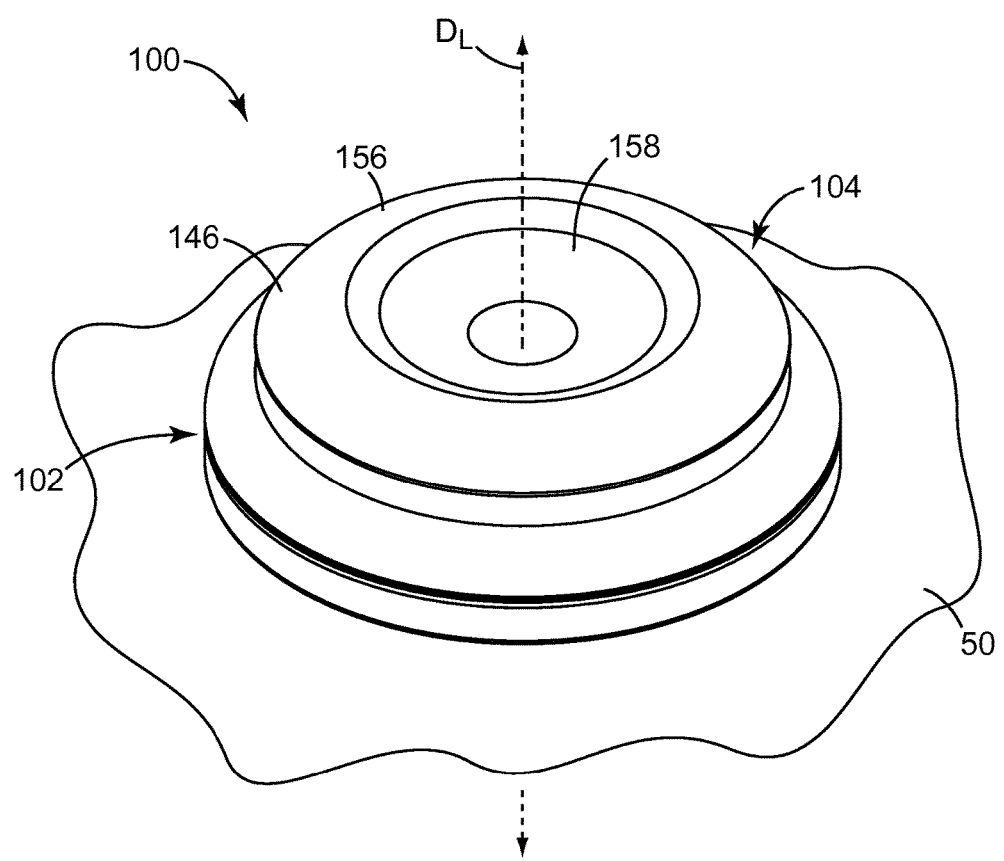
FIG. 1 is a front perspective view of an applicator according to one embodiment of the present disclosure, the applicator shown actuated and coupled to a skin surface.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. Furthermore, terms such as "front," "rear," "top," "bottom," "upward," "downward," "under," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to an applicator and method for applying a microneedle device, comprising an array of microneedles, to skin (or a biological membrane) to treat the skin (i.e., create small holes or perforations or micropores in the skin) and/or to deliver an active agent to the skin. Particularly, applicators of the present disclosure can be configured to be locked in an actuated state for a desired treatment and/or delivery period to hold the microneedle device in an actuated (or extended, or treatment) position, where at least a portion of the microneedle device extends beyond a skin-contacting surface or base of the applicator. In some embodiments, actuating the applicator and locking the applicator in the actuated state can occur simultaneously. When the skin-contacting surface of the applicator is positioned in contact with the skin and the microneedle device is in its actuated state, the microneedle device is positioned to treat the skin. An active agent can be delivered to the skin via the microneedle device while the microneedle device is held in its actuated position. The skin-contacting surface of the applicator can include an adhesive to hold the applicator in place on the skin during the desired treatment and/or delivery period, and the entire applicator can be removed when desired, e.g., when the desired treatment and/or delivery period has expired The terms "plunger" and "actuator" generally refer to an element of the applicators of the present disclosure that change an applicator from its unactuated state to its actuated state, for example, by moving from a first position to a second position to move a microneedle device, respectively, between a first position in which the microneedle device is located within the applicator (e.g., within a housing) and recessed relative to the skin-contacting surface of the applicator, and a second position in which at least a portion of the microneedle device extends beyond the skin-contacting surface. In some embodiments, a locking mechanism can be activated or engaged when the actuator and the microneedle device are moved to their respective positions, thereby simultaneously actuating the applicator and locking the applicator in an actuated state. Said another way, in some embodiments, moving the plunger and the microneedle device to their respective second positions can actuate the applicator, and can also lock the plunger and the microneedle device in their second positions, thereby locking the applicator in its actuated state.

Some existing applicators require a specific application velocity of the microneedles to puncture skin. With applicators of the present disclosure, generally a gentle hand pressure is sufficient to achieve or overcome a threshold force necessary to actuate the applicator and lock the applicator in its actuated state.

The terms or phrases "lock," "locking mechanism," and derivatives thereof are generally used to indicate that a position (e.g., a position of a plunger or microneedle device relative to a housing) or state (e.g., an actuated state of the applicators of the present disclosure) can be maintained for a desired period of time, or indefinitely, if desired (e.g., throughout a desired treatment and/or delivery period). In some embodiments, a lock or locking mechanism may be irreversible, such that it cannot be disengaged after being engaged. However, in some embodiments, a lock or locking mechanism can be reversible, such that the lock can be disabled or disengaged when desired, but generally will not revert to a disengaged state without external forces or influences acting upon it. It should be noted, however, that in the present disclosure, the terms or phrases "lock," "locking mechanism," and derivatives thereof generally do not refer to a mere shape-change, inversion, or re-configuration of a component of the applicator, such as a housing. Rather, in the present disclosure, a "lock" refers to an explicit act, device or mechanism that is employed to maintain the applicator in an actuated state, e.g., to maintain a microneedle device in a treatment and/or delivery position (e.g., relative to a housing).

In discussing the applicators of the present disclosure, the term "downward," and variations thereof, is sometimes used to describe the direction in which microneedles are pressed into skin, and "upward" to describe the opposite direction. However, those of skill in the art will understand that the applicators can be used where the microneedles are pressed into skin at an angle to the direction of the earth's gravity, or even in a direction contrary to that of the earth's gravity, and these terms are only used for simplicity and clarity to describe relative directions.

Figure 2:
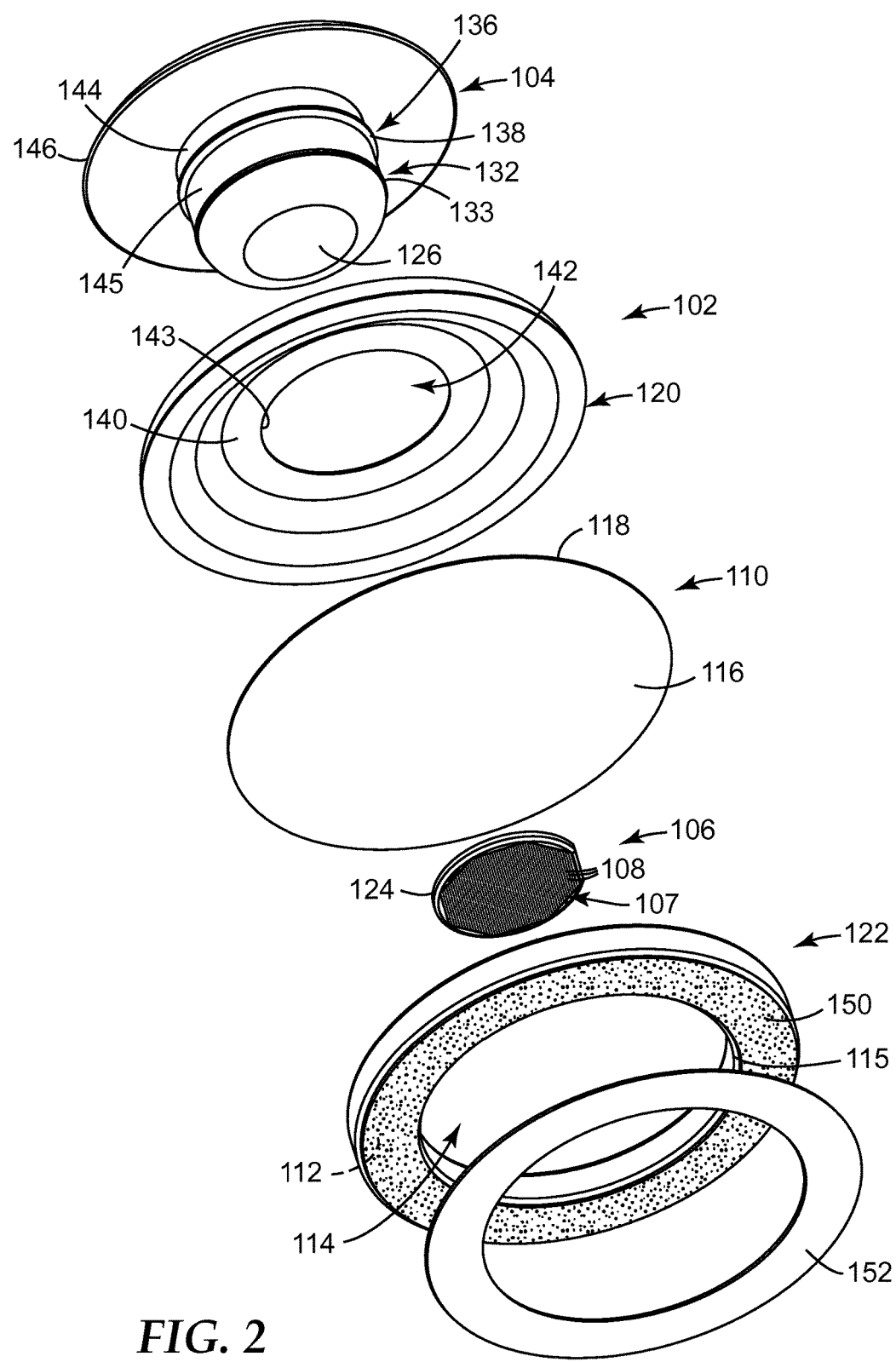
FIG. 2 is an exploded rear perspective view of the applicator of FIG. 1, the applicator including a plunger, a housing, a deformable sheet, and a microneedle device comprising a microneedle array.
Figure 3:
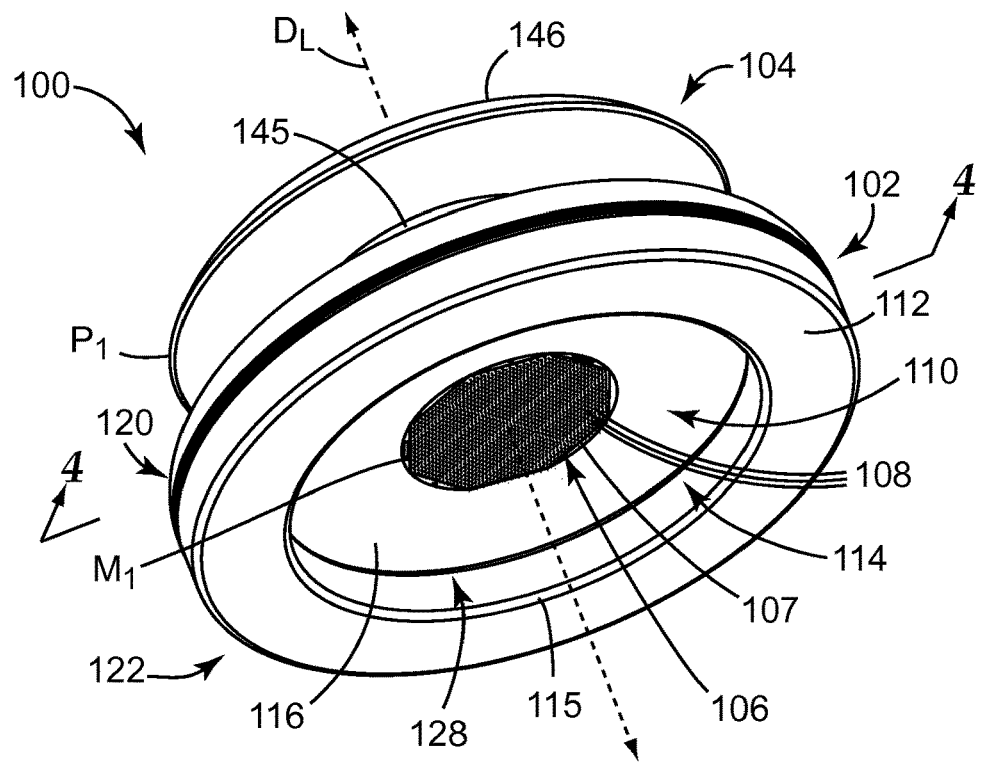
FIG. 3 is an assembled rear perspective view of the applicator of FIGS. 1 and 2, the applicator shown unactuated.
Figure 4:
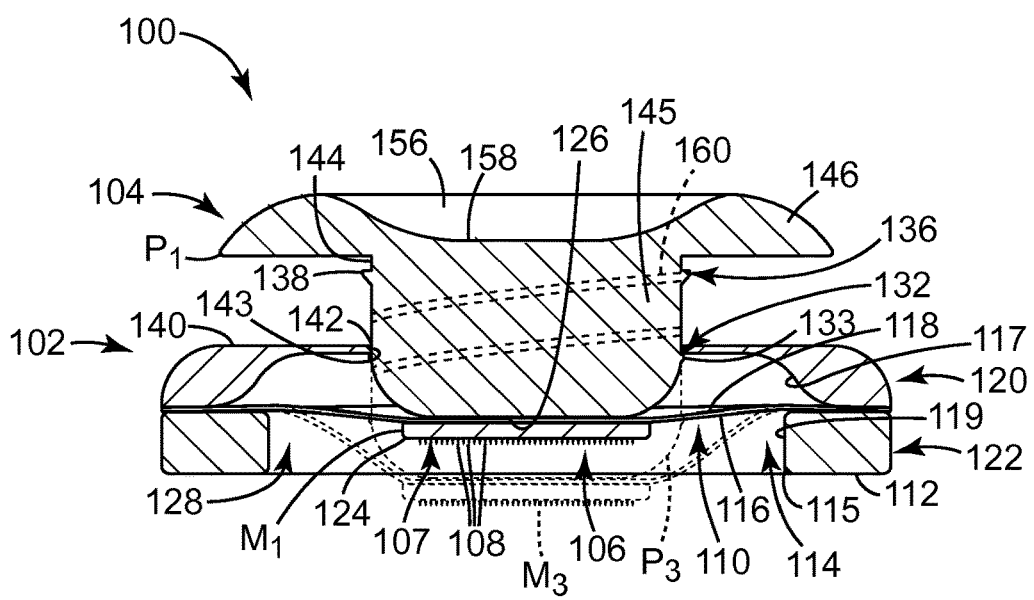
FIG. 4 is a side cross-sectional view of the applicator of FIGS. 1-3, taken along line 4-4 of FIG. 3, the applicator shown unactuated.
Figure 5:
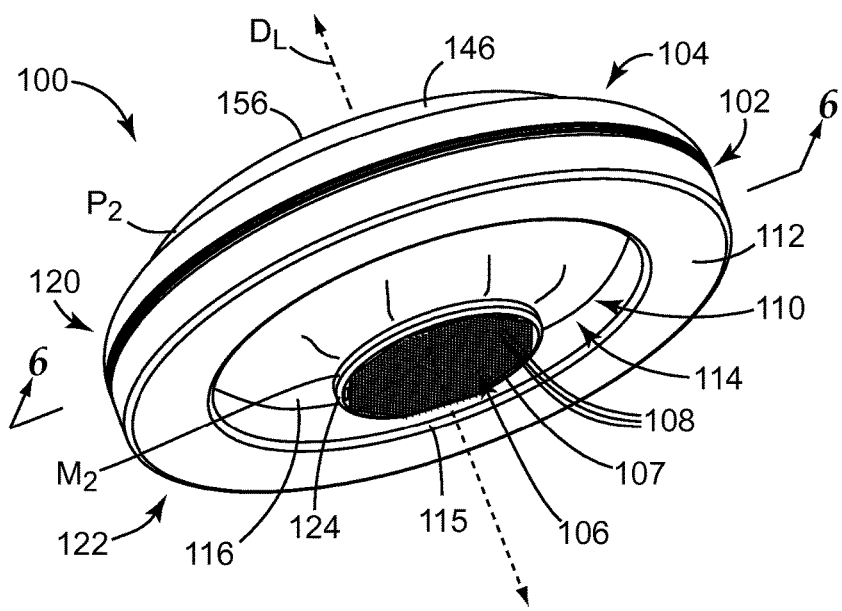
FIG. 5 is an assembled rear perspective view of the applicator of FIGS. 1-4, the applicator shown actuated.
Figure 6:
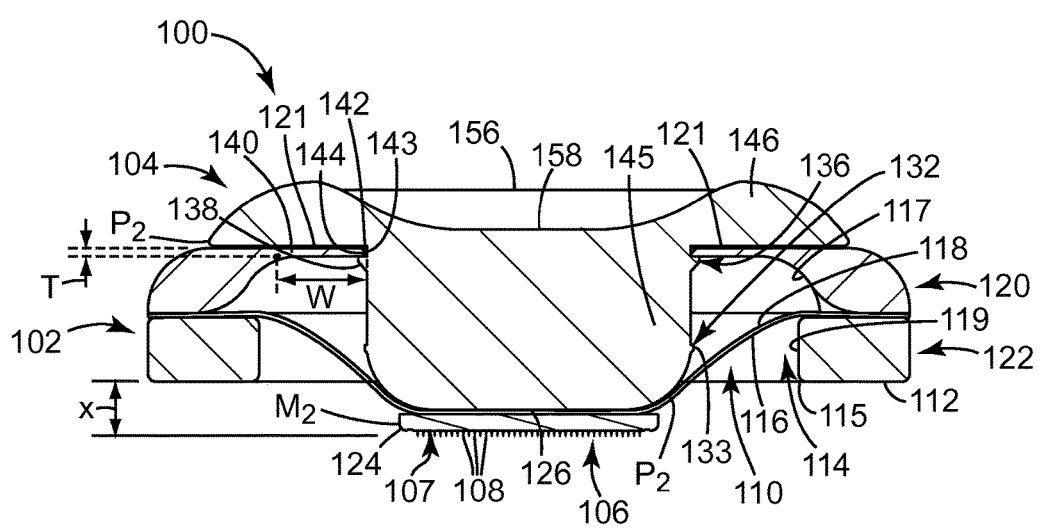
FIG. 6 is a side cross-sectional view of the applicator of FIGS. 1-5, taken along line 6-6 of FIG. 5, the applicator shown actuated.

FIGS. 1-6 illustrate an applicator 100 according to one embodiment of the present disclosure. FIGS. 1, 5 and 6 show the applicator 100 in an actuated (or activated, or treatment) state, and FIGS. 3-4 show the applicator 100 in an unactuated (or inactivated) state. FIG. 1 shows the applicator 100 actuated and coupled to skin, or a skin surface, 50.

The applicator 100 can include a housing 102, a plunger (or actuator) 104, a microneedle device 106 (comprising an array 107 of microneedles 108), and a deformable sheet 110. In some embodiments, the microneedles 108 can be configured to treat skin (i.e., create small holes or perforations or micropores in the skin) and/or deliver an active agent via skin, particularly, mammalian skin, and particularly, transdermally. Various microneedles that can be employed in applicators and methods of the present disclosure are described in greater detail below.

The term "transdermally," and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

In some embodiments, the housing 102 can include a first, skin-contacting, surface (or base) 112, which can be generally planar and configured to be positioned toward the skin surface 50. The housing 102 can further include or define a bore (or recess, channel, cavity, etc.) 114 that extends through the first surface 112 and opens to the first surface 112 at an aperture 115. The housing 102, and particularly, the bore 114 (or a portion thereof) can be configured to house at least a portion of the microneedle device 106 prior to actuation of the applicator 100.

The deformable sheet 110 can be positioned to extend across at least a portion of the bore 114 of the housing 110, such that the deformable sheet 110 is spaced a distance from the first surface 112 of the housing 102 and is generally held at a fixed vertical, or longitudinal, position with respect to a longitudinal direction $D_L$ of the bore 114 (or the applicator 100). That is, the deformable sheet 110 can be held (e.g., fixed, pinned, etc.) at one or more locations spaced a distance from the first surface 112 of the housing 102. The deformable sheet 110 can include a first side 116 oriented toward the first surface 112 of the housing 102 (i.e., positioned to face the skin surface 50) and a second side 118 opposite the first side 116.

In some embodiments, the deformable sheet 110 can be positioned to extend across an upper portion of the bore 114, e.g., located at an opposite end of the bore 114 from the aperture 115 and the first surface 112. In some embodiments, as shown in the embodiment illustrated in FIGS. 1-6, the housing 102 can include a first (e.g., upper) portion 120 and a second (e.g., lower) portion 122 that can be coupled together to retain (e.g., sandwich) the deformable sheet 110 therebetween in such a way that the deformable sheet 110 is generally held at a fixed vertical position with respect to the longitudinal direction $D_L$. In such embodiments, the deformable sheet 110 can still be considered to extend across an upper portion of the bore 114. That is, in some embodiments, the second portion 122 of the housing 102 can include or define the bore 114, and the bore 114 may also align at least partially with a bore in the first portion 120 of the housing 102. In some embodiments, the deformable sheet 110 can be considered to extend across the bore 114 at an intermediate location within the housing 102. That is, in some embodiments, as shown in FIGS. 4 and 6, the bore 114 may include a first (upper) portion 117 that is defined by at least a portion of the first portion 120 and a second (lower) portion 119 that is defined by at least a portion of the second portion 122 of the housing 102.

The "microneedle device" 106 can also be referred to as a "microneedle array assembly" and can include the array 107 of microneedles 108 (or, collectively, the "microneedle array" 107) and any supporting structure or substrate used to support the microneedle array 107 and/or to couple the microneedle array 107 to other structures or components of the applicator 100. For example, in some embodiments, the "microneedle device" or "microneedle array assembly" 106 can refer to the microneedle array 107, and a carrier (or "array carrier") 124 (see FIGS. 2, 4 and 6).

In some embodiments, the microneedle array 107 can be coupled to the carrier 124 by a variety of coupling means, including, but not limited to, press-fit or friction-fit engagement, snap-fit engagement, magnets, hook-and-loop fasteners, adhesives, cohesives, clamps, heat sealing, stitches, staples, screws, nails, rivets, brads, crimps, welding (e.g., sonic (e.g., ultrasonic) and/or thermal welding), any thermal bonding technique (e.g., heat and/or pressure applied to one or both of the components to be coupled), other suitable coupling means, or combinations thereof. Alternatively, in some embodiments, the carrier 124 and the microneedle array 107 can be integrally formed.

In some embodiments, as shown in the embodiment illustrated in FIGS. 1-6, the microneedle device 106 can be coupled to, or formed with, the first side 116 of the deformable sheet 110, such that the microneedle device 106 is (and particularly, such that the microneedles 108 are) oriented toward the first surface 112 of the housing 102, i.e., positioned to face the skin surface 50.

As shown, in some embodiments, the plunger 104 can include a shaft 145 and a cap or shroud 146 that extends outwardly (e.g., radially outwardly) relative to the shaft 145. For example, in some embodiments, the cap 146 can include an outer diameter greater than that of the shaft 145. By way of example only, the cap 146 is shown as generally have a disc or button shape, and the shaft 145 is shown is as generally having a cylindrical shape. However, it should be understood that in some embodiments, the plunger 104 does not include a cap or similar structure. In such embodiments, the plunger 104 can be generally cylindrical in shape.

The plunger 104, or at least a portion thereof (e.g., the shaft 145), can be dimensioned to be at least partially received in the bore 114 of the housing 102. In embodiments employing the deformable sheet 110, the plunger 104 (e.g., a first end 126 thereof, which can be provided by the shaft 145) can be positioned adjacent the second side 118 of deformable sheet 110 and located opposite the deformable sheet 110 from the microneedle device 106.

The plunger 104 can be movable relative to the housing 102, e.g., relative to the bore 114 in the housing 102, between a first (recessed or unlocked) position $P_1$ (see FIGS. 3 and 4) and a second (treatment or locked) position $P_2$ (see FIGS. 5 and 6) to move the microneedle device 106, respectively, between:

(i) a first position $M_1$ (see FIGS. 3 and 4) in which the microneedle device 106 is located within the bore 114 of the housing 102 (or within a pocket or recess 128 (see FIGS. 3 and 4) defined by the housing 102 (e.g., the second portion 122 of the housing 102) and the deformable sheet 110, e.g., the first side 116 of the deformable sheet 110) and recessed relative to the first surface 112 of the housing 102, such that the microneedle device 106 is located away from the skin surface 50; and (ii) a second position $M_2$ (see FIGS. 5 and 6) in which at least a portion of the microneedle device 106 (e.g., the microneedle array 107 or a portion thereof) extends through the aperture 115 and beyond the first surface 112 of the housing 102 (i.e., penetrating the skin 50, if the applicator 100 is positioned adjacent the skin 50).

The second position $M_2$ can be determined such that the microneedle device 106 extends a desired distance X (see FIG. 6) beyond the first surface 112 (and a desired distance into the skin 50 when the applicator 100 is applied to the skin 50). In some embodiments, the distance X can be the distance between the first surface 112 of the housing 102 (or a tangent thereof, if not flat) and the tips of the microneedles 108.

In some embodiments in which the bore 114 includes a first portion 117 and a second portion 119, as shown in FIGS. 4 and 6, the plunger 104 can reside in at least the first portion 117 when the plunger 104 is in its first position $P_1$ and can reside in at least the second portion 119 when the plunger 104 is in its second position $P_2$. In some embodiments, as further shown in FIGS. 4 and 6, the microneedle device 106 can reside in the second portion 119 of the bore 114 when the plunger 104 and the microneedle device 106 are in their respective first positions $P_1$, $M_1$.

The deformable sheet 110 can have a first (e.g., undeformed, unstretched, relaxed, etc.) state (see FIGS. 3 and 4) and a second (e.g., deformed, stretched, etc.) state (see FIGS. 5 and 6). As shown in FIGS. 3-4, the deformable sheet 110 is generally in its first state when the plunger 104 and the microneedle device 106 are in their respective first positions $P_1$, $M_1$, and as shown in FIGS. 5 and 6, the deformable sheet 110 is generally in its second state when the plunger 104 and the microneedle device 106 are in their respective second positions $P_2$, $M_2$. The deformable sheet 110 can be biased towards its first state, such that the deformable sheet 110 biases the plunger 104 and the microneedle device 106 toward their respective first positions $P_1$, $M_1$, which creates a certain amount of resistance against which a user must apply a force to move the plunger 104 and the microneedle device 106 out of their respective first positions $P_1$, $M_1$. That is, in embodiments employing the deformable sheet 110, in order to move the plunger 104 and the microneedle device 106 out of their respective first positions $P_1$, $M_1$, the force applied has to be sufficient to overcome the bias in the deformable sheet 110.

In some embodiments, as mentioned above, the bore 114 (and, optionally, the applicator 100 as a whole) can include the longitudinal direction or axis $D_L$ (see FIGS. 1, 3 and 5), and the plunger 104 can be movable in the bore 114 along the longitudinal direction $D_L$, which in use, is oriented generally orthogonally to the skin surface 50.

In some embodiments, the plunger 104 (e.g., the shaft 145 of the plunger 104) and the microneedle device 106 can be coupled together (e.g., directly or indirectly) and movable together, such that the first position $P_1$ of the plunger 104 corresponds to the first position $M_1$ of the microneedle device 106, and the second position $P_2$ of the plunger 104 corresponds to the second position $M_2$ of the microneedle device 106. That is, in the embodiment illustrated in FIGS. 1-6, the plunger 104 (or the first end 126 thereof) can be coupled to the second side 118 of the deformable sheet 110, so that the plunger 104, the deformable sheet 110 and the microneedle device 106 can move together.

In some embodiments, the microneedle device 106 (e.g., the carrier 124) can be coupled to the first side 116 of the deformable sheet 110, and the plunger 104, or the first end 126 thereof, can be positioned and configured to press against the second side 118 of the deformable sheet 110. In such embodiments, the plunger 104 need not be coupled to the deformable sheet 110 (indirectly or directly), but the plunger 104 does remain in contact with the deformable sheet 110, particularly, in the second position $P_2$ so as to maintain the microneedle device 106 in its second position $M_2$ for a desired period of time.

In some embodiments in which the plunger 104 is coupled to the microneedle device 106, the plunger 104 can be directly coupled to, or integrally formed with, at least a portion of the microneedle device 106, e.g., in embodiments not employing a deformable sheet 110, as described in greater detail below with respect to FIGS. 10 and 11. In such embodiments, the microneedle device 106 can extend or protrude from the plunger 104, particularly, from the first end 126 of the plunger 104. In some embodiments, the plunger 104 can be indirectly coupled to the microneedle device 106, such as via the carrier 124 and/or the deformable sheet 110. Other layers or substrates may instead, or also, be present between the plunger 104 and the microneedle device 106 for indirect coupling of the plunger 104 and the microneedle device 106.

In embodiments in which the bore 114 is defined by the second portion 122 of the housing 102, the plunger 104 can be dimensioned to also at least partially be received in a cavity defined by the first portion 120 of the housing 102. Such a cavity can be aligned at least partially with (e.g., in some embodiments, concentric with) the bore 114. Whether the plunger 104 is considered be received in the bore 114 or the bore 114 and/or an additional cavity, the plunger 104 can be inhibited from being removed from the housing 102 by one or more retaining features 132. By way of example only, in the embodiment of FIGS. 1-6, the retaining feature 132 includes a first (circumferential or annular) flange (or detent) 133 located toward the first end 126 of the plunger 104 and dimensioned to inhibit the plunger 104 from being completely removed from the housing 102, e.g., when the plunger 104 is in the first position $P_1$. As shown in FIGS. 4-6, in some embodiments, the housing 102 (e.g., the first portion 122 of the housing 102) can include an upper (annular) wall 140 that defines an aperture 142 through which the plunger 104 passes. As a result, the first flange 133 and the aperture 142 can be configured and dimensioned to inhibit the plunger 104 from being removed from the housing 102 after it has been positioned in the housing 102. The upper wall 140 of the housing 102 and the first flange 133 of the plunger 104 can engage in a variety of types of engagement, such as press-fit-type engagement, a snap-fit-type engagement, or the like, or combinations thereof.

The applicator 100 can further include a locking mechanism 136. In the embodiment illustrated in FIGS. 1-6, the locking mechanism 136 is a part of the plunger 104, however, this need not always be the case. As shown in FIGS. 2, 4 and 6, the plunger 104 (and the locking mechanism 136) can include a second (circumferential or annular) flange (or detent) 138 which is dimensioned and configured such that the plunger 104 can be depressed and moved downwardly (e.g., toward skin, when positioned adjacent skin) into the housing 102, against any resistance of the deformable sheet 110 (if employed), and snapped into the second position $P_2$. The locking mechanism 136 can therefore include the upper wall 140 of the housing 102 and the second flange 138 of the plunger 104, which can engage in a variety of types of engagement, such as press-fit-type engagement, a snap-fit-type engagement, or the like, or combinations thereof.

When a force (e.g., a downward force when the applicator 100 is being actuated) is applied that is sufficient to overcome, or exceed, a threshold force necessary to force the second flange 138 past the upper wall 140 of the housing 102, the upper wall 140 can be seated in a recess or channel 144 (e.g., an annular recess) formed in an outer surface of the plunger 104. By way of example only, the plunger 104 includes a cap or shroud 146, and in some embodiments, as shown in FIGS. 4 and 6, the recess 144 can be defined by an outer (circumferential) surface of the plunger 104, a bottom surface of the cap 146, and the second flange 138. As such, the upper wall 140 of the housing 102, the second flange 138, and the plunger cap 146 (e.g., a bottom surface thereof) can be configured such that the upper wall 140 of the housing 102 is seated in the recess 144 when the plunger 104 is pressed a sufficient distance, and with sufficient force, to overcome the resistance between the second flange 138 and the aperture 142 (see FIG. 6). The threshold force can be controlled, for example, by the interference fit and relative sizing between the second flange 138 and the aperture 142. In some embodiments, the applicator 100 can be actuated by another device, but ease and simplicity of use can be achieved when the applicator 100 is configured to allow the locking mechanism 136 to be engaged using only manual pressure.

In some embodiments, the first flange 133 can be smaller (e.g., in height and/or in depth, or distance from an outer (circumferential) surface of the plunger 104) than the second flange 138, such that during assembly, the plunger 104 can be forced into the aperture 142 with sufficient force to force the first flange 133 past the aperture 142 but not sufficient force to overcome the second flange 138, such that the plunger 104 is not accidentally moved into its second position $P_2$ when the applicator 100 is being assembled.

As shown, in some embodiments, the second flange 138 can include a ramped surface (e.g., upwardly ramped) and a substantially flat upper surface to facilitate moving the plunger 104 into the second position $P_2$ while inhibiting movement of the plunger 104 from the second position $P_2$ after the plunger 104 has been positioned in the second position $P_2$.

As shown in FIGS. 5 and 6, the locking mechanism 136 can lock the plunger 104 in its second position $P_2$ and the microneedle device 106 in its second position $M_2$. In the embodiment illustrated in FIGS. 1-6, locking the plunger 104 in its second position $P_2$ inherently and automatically locks the microneedle device 106 in its second position $M_2$. The microneedle device 106 can then remain in the second position $M_2$ for a desired treatment and/or delivery period.

As shown in FIG. 2, in some embodiments, the first surface 112 of the housing 102 can include a skin-contact adhesive 150, and the applicator 100 can further include an optional release liner 152 (see FIG. 2), which can protect the skin-contact adhesive 150 prior to use and during assembly, storage and shipment of the applicator 100. The release liner 152 can be removed prior to applying the applicator 100 to skin. The release liner 152 can be configured to release, or can be configured to present release characteristics to, the skin-contact adhesive 150, so that the applicator 100 can be coupled to the release liner 152 during storage and shipment, and can be easily removed from the release liner 152 during application of the applicator 100.

By way of example only, the applicator 100 is shown as having a generally circular cross-sectional shape, e.g., when a cross-section is taken transverse to the longitudinal direction $D_L$. As such, the first surface 112 and the release liner 152 are substantially annular, or ring-shaped. However, it should be understood that this need not be the case, and the applicator 100 can instead include a variety of cross-sectional shapes, including, but not limited to, parallelipipedal (e.g., square, rectangular, etc.), triangular, trapezoidal, polygonal (e.g., hexagonal, octagonal, etc.), etc., or combinations thereof. In addition, terms such as "radial," "circumferential," and "annular" are used herein as relative terms (e.g., relative to a center of the applicator 100 or a component thereof) and are not intended to limit the shape of the applicator 100 or components thereof to circular shapes. As a result, the term "annular" or derivations thereof can refer to a structure having an outer edge and an inner edge, such that the inner edge defines an opening (e.g., the aperture 115 into the bore 114). For example, an annular first surface 112 can have a circular or round shape (e.g., a circular ring) or any other suitable shape, including, but not limited to, triangular, rectangular, square, trapezoidal, polygonal, etc., or combinations thereof. Furthermore, an "annulus" of the present invention need not necessarily be symmetrical, but rather can be an asymmetrical or irregular shape; however, certain advantages may be possible with symmetrical and/or circular shapes.

During application of the applicator 100, the first surface 112 (i.e., the skin-contact adhesive 150) can be adhered to a desired area of the skin 50, and the applicator 100 can be actuated to treat the skin 50 and/or deliver an active agent to the skin 50. To actuate the applicator 100, the plunger 104 can be depressed to move the plunger 104 to its second position $P_2$ and lock the plunger 104 in its second position $P_2$, thereby moving the microneedle device 106 to its second position $M_2$ and locking the microneedle device 106 in its second position $M_2$. When the desired treatment and/or delivery period has lapsed, the entire applicator 100 can be removed from the skin 50 by peeling the first surface 112 (e.g., the skin-contact adhesive 150) from the skin 50. Alternatively, the skin-contact adhesive 150 can be configured to lose its adhesiveness, or tack, after a predetermined period of time, such that the applicator 100 essentially falls off of the skin 50 when it is desired for the applicator 100 to be removed.

In some embodiments, the deformable sheet 110 can be elastic, such that the deformable sheet 110 can act like a spring, can return to its undeformed (e.g., flat) configuration when a force is released, and can facilitate applying a desired active agent to the microneedles 108 (e.g., when solid microneedles are employed), for example, prior to storage, shipment, and/or assembly of the applicator 100, as described below. That is, the deformable sheet 110 can provide a bias toward the first position (e.g., $P_1$, $M_1$) of the plunger 104 and the microneedle device 106. Such a bias can facilitate returning the microneedle device 106 from its application position (e.g., a third position, as described below) to its first position $M_1$ (or another position located within the housing 102—it need not be returned to the exact same first position $M_1$) prior to applying the applicator 100 to a patient's skin.

In some embodiments, the plunger 104 can be moveable to a third (unlocked or coating) position $P_3$ (see FIG. 4) that is located intermediately of the first position $P_1$ and the second position $P_2$ and with which no locking mechanism is associated, such that the plunger 104 can be moved from the first position $P_1$ to the third position $P_3$ to correspondingly move the microneedle device 106 from its first position $M_1$ to a third position $M_3$ (see FIG. 4). In the third position $M_3$ of the microneedle device 106, at least a portion of the microneedle device 106 (e.g., at least a portion of the microneedles 108) can extend beyond the first surface 112 of the housing 102 to be exposed for application of an active agent to at least some of the microneedles 108 (e.g., by coating, dipping, brushing, etc., or combinations thereof). The elastic qualities of the deformable sheet 110 can then be exploited to facilitate returning the plunger 104 and the microneedle device 106 to their respective first positions $P_1$, $M_1$ (or a position approximately the same as the first positions $P_1$, $M_1$, i.e., another position located within the housing 102) when the force used to move the plunger 104 and the microneedle device 106 from their respective first positions $P_1$, $M_1$ to their respective third positions $P_3$, $M_3$ is removed.

Alternatively, or additionally, in some embodiments, an active agent can be applied to the microneedle device 106 (e.g., on the plunger 104, or prior to being coupled to the plunger 104) in production, and the microneedle device 106 comprising the active agent (e.g., post-coating) can then be assembled into the applicator 100. However, the application method described above that exploits the third position $P_3$, $M_3$ can simplify assembly of the applicator 100, as well as the handling of the components of the applicator 100 during assembly.

As a result, in some embodiments, the second position $P_2$, $M_2$ of the plunger 104 and/or the microneedle device 106 is a locked position in which the locking mechanism 136 is inherently or automatically activated, and the third position $P_3$, $M_3$ of the plunger 104 and/or the microneedle device 106 is an unlocked position located intermediately of the first position $P_1$, $M_1$ and the second position $P_2$, $M_2$ in which at least a portion of the microneedle device 106 extends beyond the first surface 112 of the housing 102 but in which the locking mechanism 136 is not activated. Said another way, in some embodiments, the force necessary to move the plunger 104 and/or the microneedle device 106 to their respective third positions $P_3$, $M_3$ is not sufficient to activate the locking mechanism 136 (e.g., overcome the detent of the second flange 138), but the force necessary to move the plunger 104 and/or the microneedle device 106 to their respective second positions $P_2$, $M_2$ is sufficient to activate the locking mechanism 136.

In some embodiments, the vertical distance on the plunger 104 between the first flange 133 and the second flange 138 can also be controlled to allow the microneedle device 106 to be positioned beyond the first surface 112 of the housing 102 without engaging the locking mechanism 136. In such embodiments, the second position $P_2$, $M_2$ of the plunger 104 and/or the microneedle device 106 can be at least partially defined by the location of the second flange 138 along the length of the plunger 104.

In the embodiment illustrated in FIGS. 1-6, the second position $P_2$ is a discrete and defined position. However, in some embodiments, the first position $P_1$, $M_1$ of the plunger 104 and the microneedle device 106 and/or the third position $P_3$, $M_3$ may not be discrete and defined positions, but rather may be approximate positions. For example, the plunger 104 and/or the microneedle device 106 may not return exactly to the position at which it was located initially, before being moved to the third position $P_3$, $M_3$; however, the plunger 104 and/or the microneedle device 106 will return to a position where the microneedle device 106 does not extend beyond the first surface 112 of the housing 102 and the microneedle device 106 is located, i.e., recessed, within the housing 102. Similarly, the third position $P_3$, $M_3$ of the plunger 104 and/or the microneedle device 106 may not be the exact same position every time, but the third position $P_3$, $M_3$ simply refers to a position (e.g., an unlocked position) at which at least a portion of the microneedle device 106 extends beyond the first surface 112 of the housing 102 such that at least a portion of the microneedles 108 is exposed for application of an active agent.

In some embodiments, the deformable sheet 110 can include some level of tension and therefore provide resistance to moving the plunger 104 and/or the microneedle device 106 from the first position $P_1$, $M_1$ to either the second position $P_2$, $M_2$ or the third position $P_3$, $M_3$. As a result, in such embodiments, in order to move the plunger 104 and/or the microneedle device 106 from the first position $P_1$, $M_1$ to either the second position $P_2$, $M_2$ or the third position $P_3$, $M_3$, a user must overcome the tension in the deformable sheet 110. As a result, in the embodiment illustrated in FIGS. 1-6, in order to move the plunger 104 and/or the microneedle device 106 from the first position $P_1$, $M_1$ to the second position $P_2$, $M_2$, the user must provide sufficient force or pressure to overcome the tension in the deformable sheet 110 and to exceed the threshold force of the locking mechanism 136 (e.g., to overcome the detent 138, i.e., the snap-type-engagement between the second flange 138 and the aperture 142). That is, locking the applicator 100 in its actuated state can include engaging the locking mechanism 136 as well as deforming the deformable sheet 110 a sufficient amount to allow the locking mechanism 136 to be engaged. Such force can be provided by the user pressing downwardly (i.e., toward the first surface 112 and toward skin, when the applicator 100 is positioned adjacent skin) on a second end 156 of the plunger 104, which can include a depression or recess 158 to facilitate user handling or manipulation.

By way of example only, the locking mechanism 136 of the embodiment illustrated in FIGS. 1-6 is shown as including a push-button, snap-type engagement. However, it should be understood that other suitable locking mechanisms can be employed. That is, the applicator 100 be changed from an unactuated state, configuration, or position (as shown in FIGS. 3 and 4) to an actuated state, configuration, or position (as shown in FIGS. 1, 5 and 6), and a variety of locking mechanisms can be employed that function to lock the applicator 100 in its actuated state.

One advantage of the snap-type engagement locking mechanism 136 is that such a locking mechanism can provide audible and tactile feedback to a user that the applicator 100 has been actuated.

By way of example only, FIG. 4 shows that in some embodiments, the plunger 104 be threaded or can include one or more threads (or ramped surfaces) 160 (shown in dashed lines), such that the plunger 104 can be moved from its first position $P_1$ to its second position $P_2$ (and the microneedle device 106 moved from its first position $M_1$ to its second position $M_2$, respectively) by twisting or screwing the plunger 104 with respect the housing 102 and, optionally, with respect to the deformable sheet 110 (if employed). More specifically, the plunger 104 can be configured to be threaded relative to one or more of the aperture 142 and the bore 114 in the housing 102. In such embodiments, the locking mechanism 136 can be considered to be a combination of a snap-lock and a twist-lock configuration.

As shown in FIGS. 1, 5 and 6, in some embodiments, the plunger 104 and the housing 102 can be configured such that the cap 146 (if employed) of the plunger 104 is positioned flush against the upper wall 140 of the housing 102 when the plunger 104 is in the second position $P_2$. As such, when the plunger is in its second position $P_2$, the edges of the cap 146 are less likely to be caught on other objects, such that the plunger 104 is less likely to be pried away from the housing 102 after the locking mechanism 136 has been activated or engaged and accidental removal of the applicator 100 from the skin 50 or accidental disengagement of the locking mechanism 136 is inhibited. In some embodiments, the plunger 104 may not include a cap 146 (or mushroom shape), such as shown in the embodiment of FIGS. 1-6. Rather, in some embodiments, the plunger 104 may include a variety of other shapes, such as a cylinder with no cap. In such embodiments, the plunger 104 can be sized such that when the plunger 104 is in its second position $P_2$, the second end 156 of the plunger 104 (i.e., not defined by a cap 146) can be located within the bore 114 or flush with the upper wall 140 of the housing 102, such that the plunger 104 does not include any free surfaces that can be easily grasped or pried away from the housing 102 to disengage the locking mechanism 136.

As mentioned above, in some embodiments, the locking mechanism 136 can be unlocked and/or disengaged if and when desired, but generally, in use, once engaged, the locking mechanism 136 will not disengage without other external forces or influences acting upon it. With reference to FIG. 5, in some embodiments, it can be possible to disengage the locking mechanism 136 if sufficient force is applied to the plunger 104 and/or the microneedle device 106 in an upward direction (i.e. toward the first position $P_1$, $M_1$ of the plunger 104 and the microneedle device 106), for example, to overcome the detent or snap-type engagement between the second flange 138 and the upper wall 140 of the housing 102.

During use or operation of the applicator 100, the first surface 112 of the housing 102 can be positioned adjacent the skin 50 of a patient when the plunger 104 and the microneedle device 106 are in their respective first positions $P_1$, $M_1$ (see FIGS. 3 and 4). In embodiments employing the skin-contact adhesive 150, the first surface 112 can be adhered to the skin 50 via the skin-contact adhesive 150. The plunger 104 can then be depressed downwardly (e.g., along the longitudinal direction $D_L$) into the housing 102 (i.e., into the bore 114) to move the plunger 104 and the microneedle device 106 toward their respective second positions $P_2$, $M_2$. When the plunger 104 has been moved a sufficient (vertical) distance toward the skin 50 and a force has been reached that is sufficient to deform the deformable sheet 110 (e.g., to change the deformable sheet 110 from a first state to a second state) and to overcome the interference between the housing 102 (e.g., an inner surface 143 defined by the aperture 142) and the second flange 138 of the plunger 104 (i.e., to engage the locking mechanism 136), the locking mechanism 136 can be engaged (or activated), and the plunger 104 and the microneedle device 106 can be locked in their respective second positions $P_2$, $M_2$ (see FIGS. 1 and 6). The applicator 100 can then remain in the actuated state with the plunger 104 and the microneedle device 106 locked in their respective second positions $P_2$, $M_2$ until a desired treatment and/or delivery period has elapsed. At that time, the entire applicator 100 can be removed from the skin 50.

In some embodiments, the diameter of the shaft 145 of the plunger 104 in relationship to the aperture 142 can be important to minimize the potential side-to-side movement of the plunger 104.

In addition, or alternatively, the dimensional aspects of the first portion 120 of the housing 102 can affect the force needed to move the plunger 104 to the second position $P_2$. For example, in some embodiments, as shown in FIG. 6, the first portion 120 of the housing 102 can include an upper thin section 121 that has a width W and a thickness T (see FIG. 6) and that can flex in response to moving the plunger 104 past this thin section. As the width W of the thin section of the first portion 120 of the housing 102 is reduced and/or the thickness T is increased, the housing 102 will generally have less give or flex in this area. As a result, the force needed to move the plunger 104 into the second position $P_2$ will generally be increased.

In embodiments in which an active agent has been applied to the microneedles 108 (e.g., by moving the plunger 104 and/or the microneedle device 106 to the third position $P_3$, $M_3$ and then moving the plunger 104 and/or the microneedle device 106 back to the first position $P_1$, $M_1$ or another suitable position at which the microneedle device 106 is located within the housing 102), moving the plunger 104 and/or the microneedle device 106 to the second position $P_2$, $M_2$, can cause at least a portion of the coated microneedle device 106 to press into (e.g., puncture) the skin surface 50.

The housing 102 and the plunger 104 can be formed of a variety of materials, including but not limited to, thermoset plastics (e.g., acetal resin available under the trade designation DELRIN® DuPont Corporation, Wilmington, Del.; other suitable thermoset plastics, or combinations thereof), thermoformable plastics (e.g., polyethylene, polypropylene, other suitable thermoformable plastics, or combinations thereof), or metals (e.g., stainless steel, aluminum, other suitable metals, or combinations thereof), or combinations thereof.

The deformable sheet 110 can be provided in the form of films and/or non-woven films formed of a variety of materials, including but not limited to, polyurethane (e.g., a polyurethane nonwoven film, such as 3M CoTran 9701 polyurethane nonwoven film, available from 3M Company, St. Paul, Minn.; a melt-blown polyurethane nonwoven film, such as 3M CoTran 9700 melt-blown polyurethane nonwoven film, available from 3M Company, etc.), polyethylene, polypropylene, ethylene vinyl acetate copolymer, other suitable films and/or nonwoven films, or combinations thereof. In addition, the deformable sheet 110 can be vented or unvented.

In some embodiments, as shown in FIG. 2, the skin-contact adhesive 150 can cover the entire first surface 112. Alternatively, in some embodiments, the skin-contact adhesive 150 can partially cover the first surface 112, e.g., including intermittent application of the skin-contact adhesive 150 to create gaps (e.g., randomly, or in a pattern), and/or a complete ring of skin-contact adhesive 150 that has a width that is less than the width of the first surface 112.

The skin-contact adhesive 150 is generally a pressure-sensitive adhesive, and particularly is a pressure-sensitive adhesive that is capable of securely but releasably adhering or bonding to skin (e.g., mammalian skin). The skin-contact adhesive 150 is also generally safe and non-toxic. Skin-contact adhesive layers will generally be selected according to the desired end use of the applicator 100. In some embodiments, the applicator 100 can include more than one skin-contact adhesive 150. Where the applicator 100 comprises more than one skin-contact adhesive layer 150, each skin-contact adhesive layer 150 may be selected independently of each other with regard to material and thickness used. Examples of suitable adhesives include acrylates, silicones, polyisobutylenes, synthetic rubber, natural rubber, and copolymers and mixtures thereof. Acrylates and silicones can be preferred skin-contact adhesives 150. In general, the skin-contact adhesive 150 should cause little or no irritation or sensitization of the skin during the intended wear period.

In some embodiments, the skin-contact adhesive 150 can be an acrylate (or methacrylate) copolymer. Acrylates will typically have an inherent viscosity greater than about 0.2 dL/g and will comprise one or more polymerized primary monomers and optionally one or more polar comonomers. Primary monomers suitable for use include alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. In some embodiments, the alkyl acrylates can include isooctyl acrylate, 2-ethylhexyl acrylate, n-butyl acrylate, and cyclohexyl acrylate. Polar monomers suitable for use can include those having hydroxyl, amide, or carboxylic, sulfonic, or phosphonic acid functionality. Representative examples include acrylamide, methacrylamide, N-vinyl-2-pyrrolidone, 2-hydroxyethylacrylate, 2-hydroxyethylmethacrylate, hydroxypropylacrylate, acrylic acid, methacrylic acid, pyrrolidonyl ethyl acrylate, and alkoxyethyl acrylates, such as 2-carboxyethylacrylate. In some embodiments, the amount by weight of polar monomer will not exceed about 40% of the total weight of all monomers in order to avoid excessive firmness of the final PSA product. Typically, polar monomers can be incorporated to the extent of about 1% to about 20% by weight. In some embodiments, the polar monomer can be acrylamide.

In some embodiments, the acrylate copolymer can comprise the reaction product of primary and polar monomers and additional optional monomers which, when present, are included in the polymerization reaction in quantities that will not render the adhesive composition non-tacky. The optional additional monomers may be added, for example, to improve performance, reduce cost, or for other purposes. Examples of such optional monomers include vinyl esters, such as vinyl acetate, vinyl chloride, vinylidene chloride, styrene, and macromonomers copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference.

Silicone or polysiloxane pressure-sensitive adhesives include pressure-sensitive adhesives which are based on two major components: a polymer, or gum, and a tackifying resin. The polysiloxane adhesive can be prepared by cross-linking the gum, typically a high molecular weight polydiorganosiloxane, with the resin, to produce a three-dimensional silicate structure, via a condensation reaction in an appropriate organic solvent. The ratio of resin to polymer can be adjusted in order to modify the physical properties of polysiloxane adhesives. Use of capped (or amine-compatible) polysiloxanes can, in some embodiments, be preferred so as to increase drug stability and reduce degradation. Further details and examples of silicone pressure-sensitive adhesives which can be useful are described in the U.S. Pat. No. 4,591,622 (Blizzard et al.); U.S. Pat. No. 4,584,355 (Blizzard et al.); U.S. Pat. No. 4,585,836 (Homan et al.); and U.S. Pat. No. 4,655,767 (Woodard et al.). Suitable silicone pressure-sensitive adhesives are commercially available and include the silicone adhesives sold under the trademarks BIO-PSA® by Dow Corning Corporation, Medical Products, Midland, Mich.

Further description of suitable adhesives may be found in U.S. Pat. No. 5,656,286 (Miranda et al.), U.S. Pat. No. 5,223,261 (Nelson et al.), and U.S. Pat. No. 5,380,760 (Wendel et al.), the disclosures of which are incorporated herein by reference. In some embodiments, the thickness of the skin-contact adhesive 150 can be at least about 10 µm, in some embodiments, at least about 20 µm, and in some embodiments, at least about 40 µm. In some embodiments, the thickness of the skin-contact adhesive 150 can be less than about 2 mm (0.07874 inch), in some embodiments, less than about 1 mm (0.03937 inch), and in some embodiments, less than about 150 microns (5906 microinches).

In some embodiments, a medical grade adhesive can be preferred for the skin-contact adhesive 150. Such a medical grade skin-contact adhesive 150 is can have physical properties and characteristics to be capable of maintaining intimate contact with the skin 50 before, during, and after actuation of the applicator 100. Securing the housing 102 to the skin 50 can aid in keeping the microneedles 108 inserted into the skin 50.

As mentioned above, in some embodiments, active ingredients or agents (e.g., drugs) can be delivered via the microneedles 108 (e.g., via solid or hollow microneedles, as described below). Examples of pharmaceutically active agents (also referred to as "drugs") that can be incorporated into the applicators of the present disclosure are those capable of local or systemic effect when administered to the skin. Some examples include buprenorphine, clonidine, diclofenac, estradiol, granisetron, isosorbide dinitrate, levonorgestrel, lidocaine, methylphenidate, nicotine, nitroglycerine, oxybutynin, rivastigmine, rotigotine, scopolamine, selegiline, testosterone, tulobuterol, and fentanyl, which are commercially available in the form of transdermal devices. Other examples include antiinflammatory drugs, both steroidal (e.g., hydrocortisone, prednisolone, triamcinolone) and nonsteroidal (e.g., naproxen, piroxicam); bacteriostatic agents (e.g., chlorhexidine, hexylresorcinol); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators; calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, acetylcholinesterase inhibitors (e.g., donepezil), elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219); anti-ulceratives such as H2 antagonists; steroidal hormones (e.g., progesterone); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, N-[4-(4-amino-2-ethyl-1H-imidazo[4,5-c]quinolin-1-yl)butyl]methanesulfonamide, and acyclovir); local anesthetics (e.g., benzocaine, propofol, tetracaine, prilocaine); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl citrate, sufentanil, hydromorphone hydrochloride); peptide hormones (e.g., human or animal growth hormones, LHRH, parathyroid hormones); cardioactive products such as atriopeptides; antidiabetic agents (e.g., insulin, exanatide); enzymes (e.g., anti-plaque enzymes, lysozyme, dextranase); antinauseants; anticonvulsants (e.g., carbamazine); immunosuppressives (e.g., cyclosporine); psychotherapeutics (e.g., diazepam); sedatives (e.g., phenobarbital); anticoagulants (e.g., heparin, enoxaparin sodium); analgesics (e.g., acetaminophen); antimigraine agents (e.g., ergotamine, melatonin, sumatriptan, zolmitriptan); antiarrhythmic agents (e.g., flecainide); antiemetics (e.g., metaclopromide, ondansetron, granisetron hydrochloride); anticancer agents (e.g., methotrexate); neurologic agents such as anxiolytic drugs; hemostatics; antiobesity agents; dopamine agonists (e.g., apomorphine); GnRH agonists (e.g., leuprolide, goserelin, nafarelin); fertility hormones (e.g., hCG, hMG, urofollitropin); interferons (e.g., interferon-alpha, interferon-beta, interferon-gamma, pegylated interferon-alpha); and the like, as well as pharmaceutically acceptable salts and esters thereof. The amount of drug that constitutes a therapeutically effective amount can be readily determined by those skilled in the art with due consideration of the particular drug, the particular carrier, and the desired therapeutic effect.

In some embodiments, peptide therapeutic agents (natural, synthetic, or recombinant) can be delivered via the microneedles 108 (e.g., via solid or hollow microneedles, as described below). Examples of peptide therapeutic agents that can be incorporated into the applicators of the present disclosure include parathyroid hormone (PTH), parathyroid hormone related protein (PTHrP), calcitonin, lysozyme, insulin, insulinotropic analogs, glatiramer acetate, goserelin acetate, somatostatin, octreotide, leuprolide, vasopressin, desmopressin, thymosin alpha-1, atrial natriuretic peptide (ANP), endorphin, vascular endothelial growth factor (VEGF), fibroblast-growth factor (FGF), erythropoietin (EPO), bone morphogenetic proteins (BMPs), epidermal growth factor (EFG), granulocyte colony-stimulating factor (G-CSF), granulocyte macrophage colony stimulating factor (GM-CSF), insulin-like growth factor (IGF), platelet-derived growth factor (PDGF), growth hormone release hormone (GHRH), dornase alfa, tissue plasminogen activator (tPA), urokinase, ANP clearance inhibitors, lutenizing hormone releasing hormone (LHRH), melanocyte stimulating hormones (alpha & beta MSH), pituitary hormones (hGH), adrenocorticotropic hormone (ACTH), human chorionic gonadotropin (hCG), streptokinase, interleukins (e.g. IL-2, IL-4, IL-10, IL-12, IL-15, IL-18), protein C, protein S, angiotensin, angiogenin, endothelins, pentigetide, brain natriuretic peptide (BNP), neuropeptide Y, islet amyloid polypeptide (IAPP), vasoactive intestinal peptide (VIP), hirudin, glucagon, oxytocin, and derivatives of any of the foregoing peptide therapeutic agents.

In some embodiments, drugs that are of a large molecular weight may be delivered transdermally. Increasing molecular weight of a drug typically can cause a decrease in unassisted transdermal delivery. Examples of such large molecules include proteins, peptides, nucleotide sequences, monoclonal antibodies, vaccines, polysaccharides, such as heparin, and antibiotics, such as ceftriaxone. Examples of suitable vaccines include therapeutic cancer vaccines, anthrax vaccine, flu vaccine, Lyme disease vaccine, rabies vaccine, measles vaccine, mumps vaccine, chicken pox vaccine, small pox vaccine, hepatitis vaccine, hepatitis A vaccine, hepatitis B vaccine, hepatitis C vaccine, pertussis vaccine, rubella vaccine, diphtheria vaccine, encephalitis vaccine, Japanese encephalitis vaccine, respiratory syncytial virus vaccine, yellow fever vaccine, recombinant protein vaccine, DNA vaccines, polio vaccine, therapeutic cancer vaccine, herpes vaccine, human papilloma virus vaccine, pneumococcal vaccine, meningitis vaccine, whooping cough vaccine, tetanus vaccine, typhoid fever vaccine, cholera vaccine, tuberculosis vaccine, severe acute respiratory syndrome (SARS) vaccine, HSV-1 vaccine, HSV-2 vaccine, HIV vaccine and combinations thereof. The term "vaccine" thus includes, without limitation, antigens in the forms of proteins, polysaccharides, oligosaccharides, or weakened or killed viruses. Additional examples of suitable vaccines and vaccine adjuvants are described in U.S. Publication No. 2004/0049150 (Dalton et al.), the disclosure of which is hereby incorporated by reference.

In another embodiment, small-molecule drugs that are otherwise difficult or impossible to deliver by passive transdermal delivery may be used. Examples of such molecules include salt forms; ionic molecules, such as bisphosphonates, including sodium alendronate or pamedronate; and molecules with physicochemical properties that are not conducive to passive transdermal delivery.

Release liners, which can be used as at least a portion the release liner 152, are available from a variety of manufacturers in a wide variety of proprietary formulations. Those skilled in the art will normally test those liners in simulated use conditions against an adhesive of choice to arrive at a product with the desired release characteristics. Liners which can be suitable for use in applicators of the present disclosure can be made of kraft papers, polyethylene, polypropylene, polyester or composites of any of these materials. The liner material can be coated with release agents or low adhesion coatings, such as fluorochemicals or silicones. For example, U.S. Pat. No. 4,472,480 (Olson), the disclosure of which is hereby incorporated by reference, describes low surface energy perfluorochemical liners. The liners can be papers, polyolefin films, or polyester films coated with silicone release materials. Examples of commercially available silicone coated release papers are POLYSLIK® silicone release papers available from Loparex (Willowbrook, Ill.).

In some embodiments, the length of time that the applicator 100 remains on the skin 50 may be an extended time, for example, from about 12 hours to about 14 days. In some embodiments, the duration of time that the applicator 100 remains on the skin 50 can be about 1 day (i.e., daily dosing), about 3 to 4 days (i.e., bi-weekly dosing), or about 7 days (i.e., weekly dosing).

In some embodiments, the duration of time that the applicator 100 remains on the skin 50 may be relatively short, for example from about 1 minute to about 1 hour, in some embodiments, from about 5 minutes to about 40 minutes, and in some embodiments, from about 5 minutes to about 20 minutes.

In some embodiments, the microneedles 108 can be solid. In such embodiments, if an active agent is to be delivered to the skin, the active agent can be applied to the microneedles 108 by the coating or application method described above, for example, by moving the plunger 104 and the microneedle device 106 to their respective third positions $P_3$, $M_3$, by applying an active agent prior to applicator assembly, etc. In some embodiments, the microneedles 108 can be hollow. In such embodiments, the applicator 100 can further include one or more supply reservoirs or chambers comprising the active agent that can be fluidly coupled to hollow channels in the microneedles 108, such that the active agent can be delivered (e.g., continuously, at a desired rate, over a desired period of time) to the skin 50 via the hollow channels in the microneedles 108. Additionally or alternatively, in some embodiments, when hollow microneedles 108 are employed, the applicator 100 can be coupled to a supply device (e.g., a syringe, a unit dose delivery device, a suitable metering pump, an infusion device for delivering an agent at a controlled rate, other suitable supply devices, or combinations thereof) that can be fluidly coupled to hollow channels in the microneedles 108 to drive delivery of the active agent through hollow channels in the microneedles 108 into the skin 50.

Microneedle arrays useful for practicing the present disclosure can have a variety of configurations and features, such as those described in the following patents and patent applications, the disclosures of which are incorporated herein by reference. One embodiment for the microneedle arrays includes the structures disclosed in U.S. Patent Application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin. Still another embodiment for the microneedle arrays includes the structures disclosed in U.S. Pat. No. 6,312,612 (Sherman et al.), which describes tapered structures having a hollow central channel. Yet still another embodiment for the microneedle arrays includes the structures disclosed in U.S. Pat. No. 6,379,324 (Garstein et al.), which describes hollow microneedles having at least one longitudinal blade at the top surface of the tip of the microneedle. A further embodiment for the microneedle arrays includes the structures disclosed in U.S. Patent Application Publication Nos. US2012/0123387 (Gonzalez et al.) and US2011/0213335 (Burton et al.), which both describe hollow microneedles. A still further embodiment for the microneedle arrays includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure.

In some embodiments, the microneedle material can be (or include) silicon, glass, or a metal such as stainless steel, titanium, or nickel titanium alloy. In some embodiments, the microneedle material can be (or include) a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In some embodiments, the microneedles can be made from (or include) a combination of two or more of any of the above mentioned materials. For example, the tip of a microneedle may be a dissolvable material, while the remainder of the microneedle is a medical grade polymeric material.

A microneedle or the plurality of microneedles in a microneedle array useful for practicing the present disclosure can have a variety of shapes that are capable of piercing the stratum corneum. In some embodiments, one or more of the plurality of microneedles can have a square pyramidal shape, triangular pyramidal shape, stepped pyramidal shape, conical shape, microblade shape, or the shape of a hypodermic needle. In some embodiments, one or more of the plurality of microneedles can have a square pyramidal shape. In some embodiments, one or more of the plurality of microneedles can have a triangular pyramidal shape. In some embodiments, one or more of the plurality of microneedles can have a stepped pyramidal shape. In some embodiments, one or more of the plurality of microneedles can have a conical shape. In some embodiments, one or more of the plurality of microneedles can have a microblade shape. In some embodiments, one or more of the plurality of microneedles can have the shape of a hypodermic needle. The shape can be symmetric or asymmetric. The shape can be truncated (for example, the plurality of microneedles can have a truncated pyramid shape or truncated cone shape). In a preferred embodiment, the plurality of microneedles in a microneedle array each have a square pyramidal shape.

In some embodiments, the plurality of microneedles in a microneedle array are solid microneedles (that is, the microneedles are solid throughout). In some embodiments, the plurality of solid microneedles in a solid microneedle array can have a square pyramidal shape, triangular pyramidal shape, stepped pyramidal shape, conical shape, or microblade shape. In a preferred embodiment, the plurality of solid microneedles in a solid microneedle array each have a square pyramidal shape.

In some embodiments, the plurality of microneedles in a microneedle array are hollow microneedles (that is, the microneedles contain a hollow bore through the microneedle). The hollow bore can be from the base of the microneedle to the tip of the microneedle or the bore can be from the base of the microneedle to a position offset from the tip of the microneedle. In some embodiments, one or more of the plurality of hollow microneedles in a hollow microneedle array can have a conical shape, cylindrical shape, square pyramidal shape, triangular pyramidal shape, or the shape of a hypodermic needle.

In some embodiments, one or more of the plurality of hollow microneedles in a hollow microneedle array can have a conical shape. In some embodiments, one or more of the plurality of hollow microneedles in a hollow microneedle array can have a cylindrical shape. In some embodiments, one or more of the plurality of hollow microneedles in a hollow microneedle array can have a square pyramidal shape. In some embodiments, one or more of the plurality of hollow microneedles in a hollow microneedle array can have a triangular pyramidal shape. In some embodiments, one or more of the plurality of hollow microneedles in a hollow microneedle array can have the shape of a hypodermic needle. In a preferred embodiment, the plurality of hollow microneedles in a hollow microneedle array each have the shape of a conventional hypodermic needle.

Figure 12:
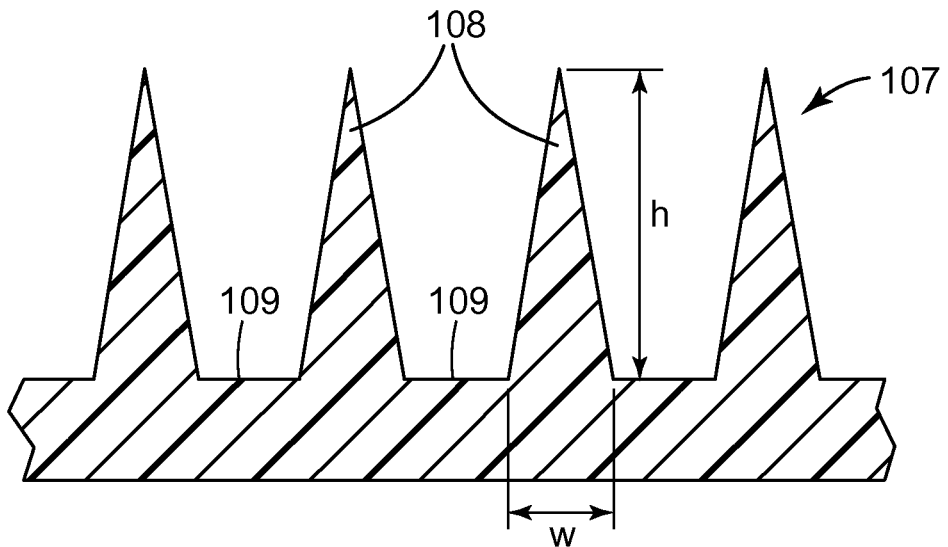
FIG. 12 is a close-up side cross-sectional view of the microneedle array of FIGS. 2-6 (shown with the microneedles pointing upwardly).

FIG. 12 shows a portion of the microneedle array 107 that includes four microneedles 108 (of which two are referenced in FIG. 12) positioned on a microneedle substrate 109. Each microneedle 108 has a height h, which is the length from the tip of the microneedle 108 to the microneedle base at substrate 109. Either the height of a single microneedle or the average height of all microneedles on the microneedle array can be referred to as the height of the microneedle, h. In some embodiments, each of the plurality of microneedles (or the average of all of the plurality of microneedles) has a height of about 100 to about 3000 micrometers, in some embodiments, about 100 to about 1500 micrometers, in some embodiments, about 100 to about 1200 micrometers, and, in some embodiments, about 100 to about 1000 micrometers.

In some embodiments, each of the plurality of microneedles (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1500 micrometers, about 500 to about 1000 micrometers, or about 500 to about 750 micrometers.

In some embodiments, each of the plurality of microneedles (or the average of all of the plurality of microneedles) has a height of about 800 to about 1400 micrometers.

In some embodiments, each of the plurality of microneedles (or the average of all of the plurality of microneedles) has a height of about 500.

In some embodiments, each of the plurality of microneedles (or the average of all of the plurality of microneedles) has a height of less than about 3000 micrometers. In other embodiments, each of the plurality of microneedles (or the average of all of the plurality of microneedles) has a height of less than about 1500 micrometers. In still other embodiments, each of the plurality of microneedles (or the average of all of the plurality of microneedles) has a height of less than about 1200 micrometers. In yet still other embodiments, each of the plurality of microneedles (or the average of all of the plurality of microneedles) has a height of less than about 1000 micrometers. In further embodiments, each of the plurality of microneedles (or the average of all of the plurality of microneedles) has a height of less than about 750 micrometers. In still further embodiments, each of the plurality of microneedles (or the average of all of the plurality of microneedles) has a height of less than about 600 micrometers.

In some embodiments, each of the plurality of microneedles (or the average of all of the plurality of microneedles) has a height of at least about 100 micrometers. In other embodiments, each of the plurality of microneedles (or the average of all of the plurality of microneedles) has a height of at least about 200 micrometers. In still other embodiments, each of the plurality of microneedles (or the average of all of the plurality of microneedles) has a height of at least about 250 micrometers. In further embodiments, each of the plurality of microneedles (or the average of all of the plurality of microneedles) has a height of at least about 500 micrometers. In still further embodiments, each of the plurality of microneedles (or the average of all of the plurality of microneedles) has a height of at least about 800 micrometers.

In some embodiments employing solid microneedles, each of the plurality of solid microneedles (or the average of all of the plurality of solid microneedles) has a height of about 100 to about 1500 micrometers, about 100 to about 1200 micrometers, about 200 to about 1000 micrometers, about 200 to about 750 micrometers, about 200 to about 600 micrometers, or about 500 micrometers.

In some embodiments employing hollow microneedles, each of the plurality of hollow microneedles (or the average of all of the plurality of hollow microneedles) has a height of about 100 to about 3000 micrometers, about 800 to about 1400 micrometers, or about 500 micrometers.

In some embodiments, each of the plurality of hollow microneedles (or the average of all of the plurality of hollow microneedles) has a height of about 900 to about 1000 micrometers. In other embodiments, each of the plurality of hollow microneedles (or the average of all of the plurality of hollow microneedles) has a height of about 900 to about 950 micrometers. In still other embodiments, each of the plurality of hollow microneedles (or the average of all of the plurality of hollow microneedles) has a height of about 900 micrometers.

A single microneedle or the plurality of microneedles in a microneedle array can also be characterized by their aspect ratio. The aspect ratio of a microneedle is the ratio of the height of the microneedle, h to the width (at the base of the microneedle), w (as shown in FIG. 12). The aspect ratio can be presented as h:w. In some embodiments, each of the plurality of microneedles (or the average of all the plurality of microneedles) has (have) an aspect ratio in the range of 2:1 to 5:1. In some of these embodiments, each of the plurality of microneedles (or the average of all of the plurality of microneedles) has (have) an aspect ratio of at least 3:1.

In some embodiments, the array of microneedles contains about 100 to about 1500 microneedles per $cm^2$ of the array of microneedles.

In some embodiments employing solid microneedles, the array of solid microneedles contains about 100 to about 1500 solid microneedles per $cm^2$ of the array of solid microneedles.

In some embodiments, the array of solid microneedles contains about 200 to about 500 solid microneedles per $cm^2$ of the array of solid microneedles.

In some embodiments, the array of solid microneedles contains about 300 to about 400 solid microneedles per $cm^2$ of the array of solid microneedles.

In some embodiments employing hollow microneedles, the array of hollow microneedles contains about 3 to about 30 hollow microneedles per array of hollow microneedles.

In some embodiments, the array of hollow microneedles contains about 10 to about 30 hollow microneedles per array of hollow microneedles.

In some embodiments, the array of hollow microneedles contains about 3 to about 20 hollow microneedles per array of hollow microneedles.

In some embodiments, the array of hollow microneedles contains about 13 to about 20 hollow microneedles per array of hollow microneedles.

In some embodiments, the array of hollow microneedles contains about 8 to about 18 hollow microneedles per array of hollow microneedles.

In some embodiments, the array of hollow microneedles contains about 18 hollow microneedles per array of hollow microneedles.

In some embodiments, the array of hollow microneedles contains about 12 hollow microneedles per array of hollow microneedles.

In some embodiments, each of the plurality of microneedles (or the average of all of the plurality of microneedles) in a microneedle array can penetrate into the skin to a depth of about 50 to about 1500 micrometers, about 50 to about 400 micrometers, or about 50 to about 250 micrometers.

In some embodiments, each of the plurality of microneedles (or the average of all of the plurality of microneedles) in a microneedle array can penetrate into the skin to a depth of about 100 to about 400 micrometers, or about 100 to about 300 micrometers.

In some embodiments, each of the plurality of microneedles (or the average of all of the plurality of microneedles) in a microneedle array can penetrate into the skin to a depth of about 150 to about 1500 micrometers, or about 800 to about 1500 micrometers.

In some embodiments, each of the plurality of microneedles (or the average of all of the plurality of microneedles) in a microneedle array can penetrate into the skin to a depth of about 400 to about 800 micrometers.

For all of the above embodiments, it will be appreciated that the depth of penetration (DOP) of each of the plurality of microneedles (or the average of all of the plurality of microneedles) in a microneedle array may not be the full length of the microneedles themselves.

Figure 13:
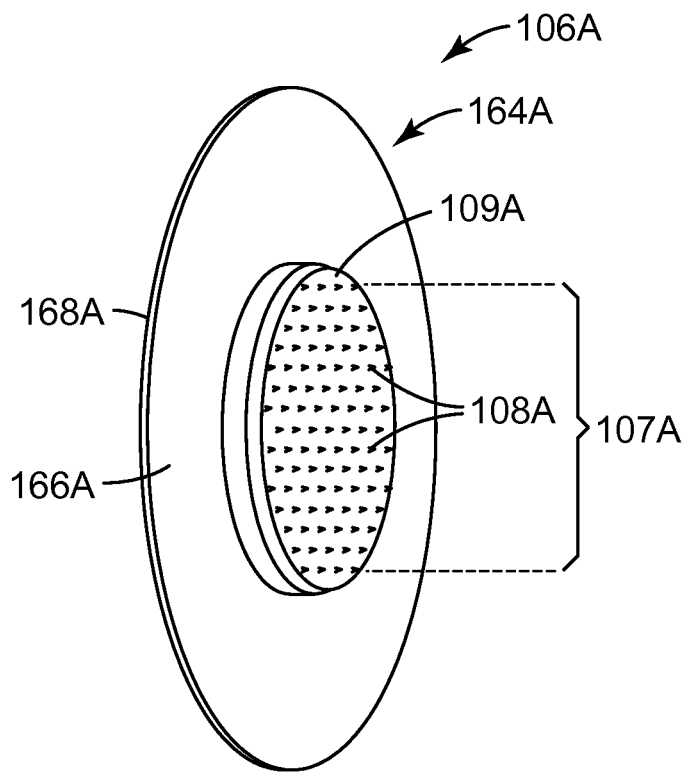
FIG. 13 is a perspective view of a microneedle device according to another embodiment of the present disclosure.

In some embodiments, the microneedle device according to the present disclosure can be in the form of a patch. One example of such an embodiment is shown in more detail in FIG. 13. FIG. 13 illustrates a microneedle device 106A comprising a patch 164A in the form of a combination of a microneedle array 107A, pressure sensitive adhesive 166A, and backing 168A. The microneedle array 107A is illustrated with microneedles 108A protruding from a microneedle substrate 109A. The microneedles 108A can be arranged in any desired pattern or distributed over the microneedle substrate 109A randomly. As shown, the microneedles 108A are arranged in uniformly spaced rows. When arranged in rows, the rows can be arranged so that the microneedles 108A are aligned or offset. In some embodiments (not shown), the microneedles 108A can be arranged in a polygonal pattern such as a triangle, square, rectangle, pentagon, hexagon, heptagon, octagon, or trapezoid. In other embodiments (not shown), the microneedles 108A can be arranged in a circular or oval pattern.

It should be understood that any description herein with respect to the microneedle device 106, the microneedle array 107, the microneedles 108, and the microneedle substrate 109 can equally apply to the microneedle device 106A, the microneedle array 107A, the microneedles 108A, and the microneedle substrate 109A, respectively, and vice versa.

In some embodiments, the surface area of the substrate 109, 109A covered with microneedles 108, 108A is about 0.1 $cm^2$ to about 20 $cm^2$. In some of these embodiments, the surface area of the substrate 109, 109A covered with microneedles 108, 108A is about 0.5 $cm^2$ to about 5 $cm^2$. In some other of these embodiments, the surface area of the substrate 109, 109A covered with microneedles 108, 108A is about 1 $cm^2$ to about 3 $cm^2$. In still other of these embodiments, the surface area of the substrate 109, 109A covered with microneedles 108, 108A is about 1 $cm^2$ to about 2 $cm^2$.

In some embodiments (e.g., as shown in FIGS. 2 and 13), the microneedles of the present disclosure can be disposed over substantially the entire surface of the array. In other embodiments (not shown), a portion of the substrate may not be provided with microneedles (that is, a portion of the substrate is non-structured). In some of these embodiments, the non-structured surface has an area of more than about 1 percent and less than about 75 percent of the total area of the device surface that faces the skin surface. In another of these embodiments, the non-structured surface has an area of more than about 0.65 $cm^2$ (0.10 square inch) to less than about 6.5 $cm^2$ (1 square inch).

For hollow microneedles, a hollow channel or bore extends through the substrate 109, 109A and microneedles 108, 108A. In some embodiments, the bore exits at a channel opening at or near the tip of the hollow microneedle. The channel preferably exits at an opening near the tip of the hollow microneedle. Most preferably, the channel or bore continues along a central axis of the microneedle, but exits similar to a hypodermic needle on a sloping side-wall of the microneedle to help prevent blockage of the channel by tissue upon insertion. In some embodiments, the diameter of the channel bore is about 10 to about 200 micrometers. In other embodiments, the diameter of the channel bore is about 10 to about 150 micrometers. In still other embodiments, the diameter of the channel bore is about 30 to about 60 micrometers.

In some embodiments of hollow microneedles, the average cross-sectional area of the channel bore is about 75 to about 32,000 micrometers. In other embodiments of hollow microneedles, the average cross-sectional area of the channel bore is about 75 to about 18,000 micrometers. In still other embodiments of hollow microneedles, the average cross-sectional area of the channel bore is about 700 to about 3,000 micrometers.

In some embodiments of hollow microneedle arrays, the average spacing between adjacent microneedles (as measured from microneedle tip to microneedle tip) is between about 0.7 mm and about 20 mm. In other embodiments of hollow microneedle arrays, the average spacing between adjacent microneedles is between about 0.7 mm and about 10 mm. In still other embodiments of hollow microneedle arrays, the average spacing between adjacent microneedles is between about 2 mm and about 20 mm. In still other embodiments of hollow microneedle arrays, the average spacing between adjacent microneedles is between about 2 mm and about 10 mm. In a preferred embodiment of hollow microneedle arrays, the average spacing between adjacent microneedles is between about 2 mm.

In some embodiments of hollow microneedle arrays, the average spacing between adjacent microneedles (as measured from microneedle tip to microneedle tip) is greater than about 0.7 mm. In other embodiments of hollow microneedle arrays, the average spacing between adjacent microneedles is greater than about 2 mm.

In some embodiments of hollow microneedle arrays, the average spacing between adjacent microneedles is less than about 20 mm. In other embodiments of hollow microneedle arrays, the average spacing between adjacent microneedles is less than about 10 mm.

In some embodiments of solid microneedle arrays, the average spacing between adjacent microneedles (as measured from microneedle tip to microneedle tip) is between about 200 micrometers and about 2000 micrometers. In other embodiments of solid microneedle arrays, the average spacing between adjacent microneedles is between about 200 micrometers and about 600 micrometers. In still other embodiments of solid microneedle arrays, the average spacing between adjacent microneedles is between about 200 micrometers and about 300 micrometers. In yet still other embodiments of solid microneedle arrays, the average spacing between adjacent microneedles is between about 500 micrometers and about 600 micrometers.

In some embodiments of solid microneedle arrays, the average spacing between adjacent microneedles (as measured from microneedle tip to microneedle tip) is greater than about 200 micrometers. In other embodiments of solid microneedle arrays, the average spacing between adjacent microneedles is greater than about 500 micrometers.

In some embodiments of solid microneedle arrays, the average spacing between adjacent microneedles is less than about 2000 micrometers. In other embodiments of solid microneedle arrays, the average spacing between adjacent microneedles is less than about 1000 micrometers. In still other embodiments of solid microneedle arrays, the average spacing between adjacent microneedles is less than about 600 micrometers. In yet still other embodiments of solid microneedle arrays, the average spacing between adjacent microneedles is less than about 300 micrometers.

The microneedle arrays can be manufactured in any suitable way such as by injection molding, compression molding, metal injection molding, stamping, photolithography, or extrusion. In one embodiment, hollow microneedle arrays can be made by thermocycled injection molding of a polymer such as medical grade polycarbonate or LCP, followed by laser drilling to form the channels of the microneedles.

Additional exemplary embodiments of applicators of the present disclosure will now be described with respect to FIGS. 7-11. FIGS. 7-11 illustrate various applicators of the present disclosure, wherein like numerals represent like elements. The applicators of FIGS. 7-11 share many of the same elements, features, and functions as those described above with respect to FIGS. 1-6. Reference is made to the description above accompanying FIGS. 1-6 for a more complete description of the features and elements (and alternatives to such features and elements) of the embodiments illustrated in FIGS. 7-11. Any of the features described above with respect to FIGS. 1-6 can be applied to the embodiments of FIGS. 7-12, and vice versa.

Figure 7:
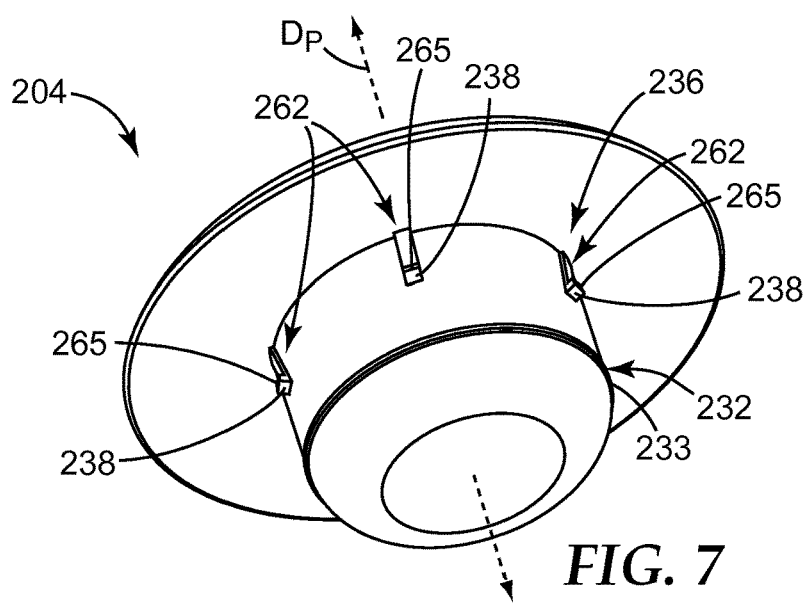
FIG. 7 is a rear perspective view of a plunger according to another embodiment of the present disclosure.

FIG. 7 illustrates a plunger 204 and a locking mechanism 236 according to another embodiment that can be employed with applicators of the present disclosure, such as, e.g., the applicator 100 of FIGS. 1-6 or the applicator 400 of FIGS. 10-11 (described below). The locking mechanism 236 is another example of a locking mechanism that can be employed on the plunger 204. As shown in FIG. 7, the locking mechanism 236 can include one or more ribs or projections 262. Each rib 262 can include an outwardly-extending (e.g., radially-outwardly-extending) portion, flange or detent 238 (e.g., a "second flange" 238). Each rib 262 can be configured to engage with another portion of an applicator, such as the housing 102 of the applicator 100, or more specifically, the aperture 142 defined by the upper annular wall 140 of the housing 102, similarly to the second flange 138 of the applicator 100. The rib 262 and/or the second flange 238 can include a cam surface 265 adapted to slide along an inner surface of a housing, such as the inner surface defined by the aperture 142 in the upper wall 140 of the housing 102 of FIGS. 1-6. The cam surface 265 of each rib 262 can cause the respective rib 262 to be forced radially inwardly as plunger 204 is moved into a housing, and further allows the respective rib 262 to snap (e.g., radially outwardly) into position under an upper wall of a housing, such as the upper wall 140 of the housing 102 of FIGS. 1-6. That is, the ribs 262, and particularly, the second flanges 238 can lock the plunger 204 in its second position P$_2$ with respect to the housing 102 in a similar manner as the second flange 138 of the applicator 100, but are included to represent that the second flange 138 need not be continuous or extend about the entire periphery or outer surface of the plunger 104, 204. Rather, in some embodiments, the second flange 238, as shown in FIG. 7, can be provided by one or more discrete or disparate elements, such as the ribs 262 shown in FIG. 7. As further shown in FIG. 7, in some embodiments, the ribs 262 can be circumferentially-spaced about an outer surface of the plunger 204 (e.g., about an outer surface of a tubular or cylindrical portion of the plunger 204).

As mentioned above, in some embodiments, the locking mechanism 236 can be unlocked and/or disengaged if and when desired, but generally, in use, once engaged, the locking mechanism 236 will not disengage without other external forces or influences acting upon it. In some embodiments, it can be possible to disengage the locking mechanism 236 if sufficient force is applied to the plunger 204 and/or a microneedle device (e.g., the microneedle device 106) in an upward direction, for example, to overcome the detent or snap-type engagement between the second flange 238 and a housing to move the rib(s) 262 inwardly and bring its cam surface 265 into contact with an inner surface of the housing, and to continue sliding the cam surface 265 upwardly along the inner surface of the housing until the second flange 238 is released from contact with the housing.

By way of example only, the plunger 204 includes a first flange 233 as a retaining feature 232 that is essentially the same as the first flange 133 (and retaining feature 132) of the applicator 100; however, it should be understood that, in some embodiments, the first flange 233 can instead be formed of one or more discrete or disparate elements, similar to the ribs 262.

Furthermore, each rib 262 is illustrated as including a portion that extends substantially longitudinally (e.g., parallel with a longitudinal direction $D_P$ of the plunger 204), with the second flange 238 that extends outwardly (e.g., radially-outwardly) therefrom. However, it should be understood that, in some embodiments, each rib 262 may include only the outwardly (e.g., radially-outwardly) projecting second flange 238. In such embodiments, the outer (i.e., peripheral, e.g., circumferential) surface of the plunger 204 may include one or more raised bumps, ribs or fins that are configured to function as the second flange(s) 238 to lock an applicator in its actuated state.

The descriptions above with respect to the applicator 100 of FIGS. 1-6 regarding use and operation of the applicator 100 and the locking mechanism 136, and configuring the interference fit, also apply equally to the plunger 204 of FIG. 7. For example, as the plunger 204 is depressed with sufficient force to overcome the detent snap-type engagement between the plurality of second flanges 238 and a housing (e.g., an inner surface, such as the inner surface 143 defined by the aperture 142), the plunger 204 can move into, and be locked into, a second position, thereby locking a microneedle device in its second position.

Figure 8:
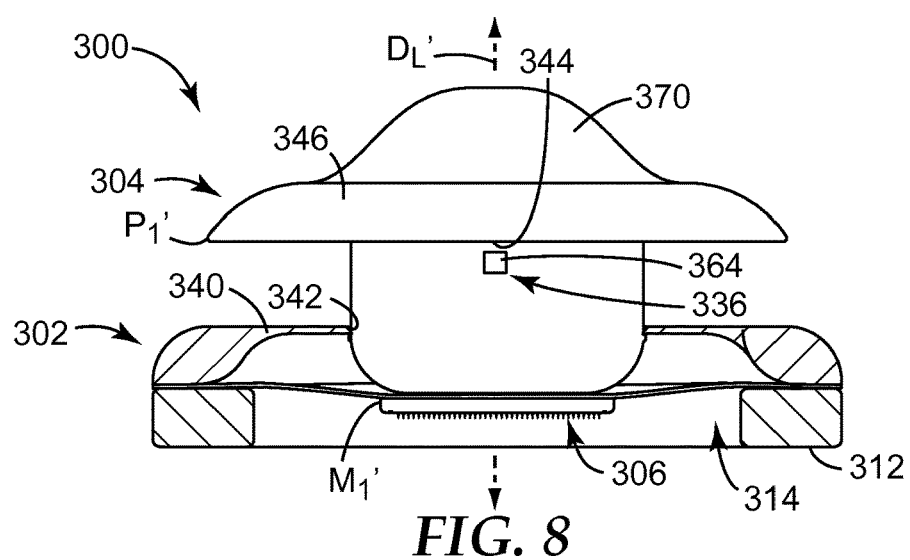
FIG. 8 is a side partial cross-sectional view of an applicator according to another embodiment of the present disclosure, the applicator shown unactuated.
Figure 9:
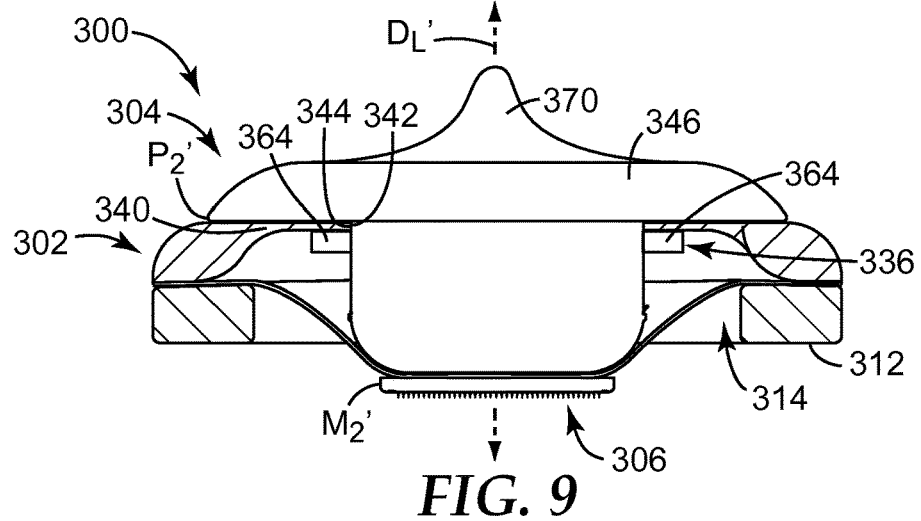
FIG. 9 is a side partial cross-sectional view of the applicator of FIG. 8, shown actuated.

FIGS. 8-9 illustrate an applicator 300 according to another embodiment of the present disclosure. The applicator 300 includes a housing 302, a plunger 304, a microneedle device 306, and a locking mechanism 336. The plunger 304 includes a cap or shroud 346. The applicator 300 is essentially the same as the applicator 100 of FIGS. 1-6, with the exception of the locking mechanism 336. Similar to the locking mechanism 136 of the applicator 100, the locking mechanism 336 includes elements of the plunger 304 and elements of the housing 302, and an interaction or interengagement therebetween. Particularly, the locking mechanism 336 includes one or more (two are illustrated by way of example) projections 364 that extend outwardly (e.g., radially-outwardly) from a periphery or outer surface (e.g., from an outer circumferential surface) of the plunger 304. Again, in the embodiment illustrated in FIGS. 8-9, the locking mechanism 336 includes a part of the plunger 304, however, this need not always be the case.

The plunger 304 and/or the housing 302 can be configured such that the plunger 304 can be rotated (or twisted) relative to the housing 302, e.g., in a bore 314 formed in the housing 302. As such, the housing 302 can be shaped and configured to allow the one or more projections 364 to move relative to the housing 302 until the plunger 304 has reached, or is close to reaching, its second position $P_2'$ (see FIG. 9), and then the plunger 304 and/or the housing 302 can be rotated about a longitudinal axis or direction $D_L'$ until the one or more projections 364 are positioned to lock the plunger 304 in its second position $P_2'$, thereby locking the microneedle device 306 in its second position $M_2'$ (see FIG. 9).

Figure 8A:
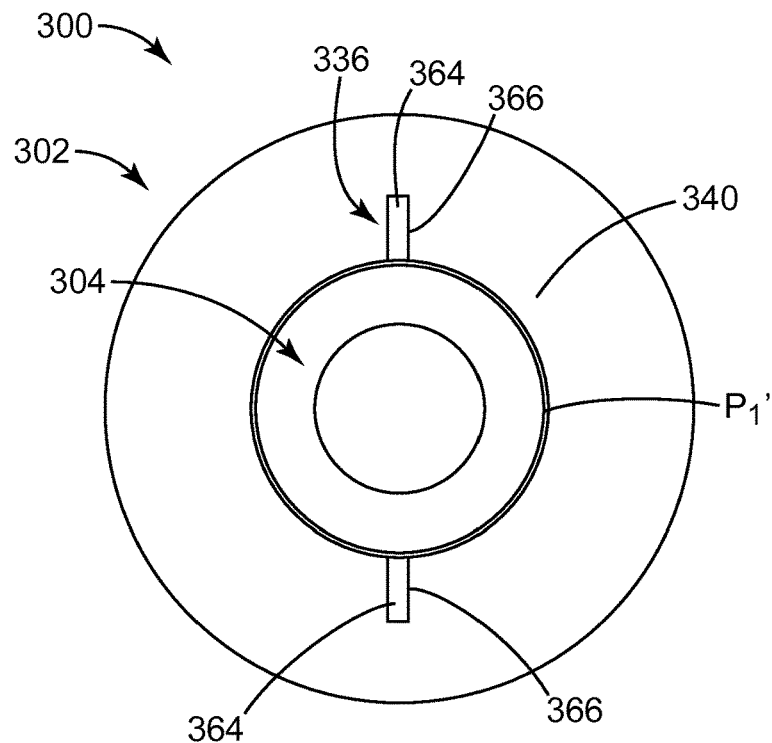
FIG. 8A is a top plan view of the applicator of FIG. 8, shown unactuated, with portions removed for clarity.
Figure 9A:
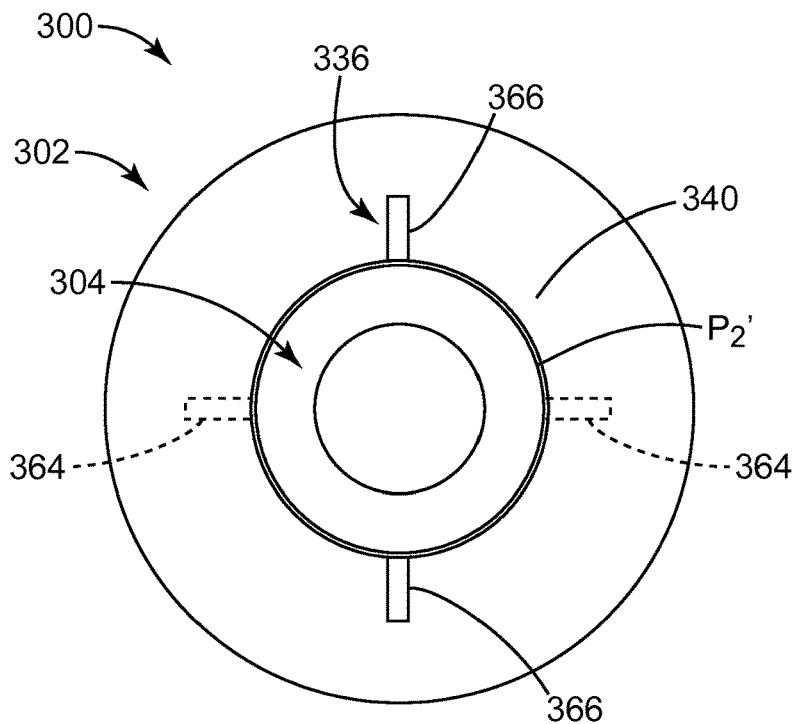
FIG. 9A is a top plan view of the applicator of FIGS. 8, 8A and 9, shown actuated, with portions removed for clarity.

For example, in some embodiments, an upper (annular) wall 340 of the housing 302 can include or define an aperture 342 that includes one or more corresponding recesses (or notches or slots) 366 (see FIGS. 8A and 9A where the cap 346 of the plunger 304 has been removed for clarity). The recesses 366 are dimensioned to allow the projections 364 to pass therethrough when the plunger 304 is moved relative to the housing 302, if the projections 364 are properly aligned with the recesses 366. When the plunger 304 and the microneedle device 306 are moved from their respective first positions $P_1'$, $M_1'$ toward their respective second positions $P_2'$, $M_2'$, the projections 364 can be aligned with such recesses 366 to pass therethrough (see FIG. 8A). After the projections 364 have passed through the recesses 366, the plunger 304 and/or the housing 302 can be rotated or twisted relative to the other to an angular position where the projections 364 are no longer aligned with the recesses 366 in the housing 302 (e.g., in the upper wall 340 of the housing 302), such that the plunger 304 and the microneedle device 306 are locked in their respective second positions $P_2'$, $M_2'$ (see FIG. 9A).

Two projections 364 and recesses 366 that are located 180 degrees apart about the periphery of the plunger 304 are shown by way of example only. However, it should be understood that such a twist-lock engaging locking mechanism 336 can include as few as one projection 364 and corresponding recess 366 or as many as desired.

FIG. 9A shows the plunger 304 rotated 90 degrees relative to the housing 302 and relative to its angular position in FIG. 8A, such that the first position $P_1'$, $M_1'$ of the plunger 304 and the microneedle device 306, respectively, and second position $P_2'$, $M_2'$ of the plunger 304 and the microneedle device 306, respectively, are separated 90 degrees from one another. However, it should be understood that the applicator 300 can be configured to be rotated less than 90 degrees or greater than 90 degrees, and that the illustrated 90-degree configuration is shown by way of example only.

In some embodiments, as shown in FIGS. 8 and 9 the plunger 304 (e.g., the cap 346) can include one or more upwardly-extending fins or projections 370 to facilitate twisting the plunger 304 to engage the locking mechanism 336 and/or to move the plunger 304 and the microneedle device 306 to their respective second positions $P_2'$, $M_2'$.

As shown in FIGS. 8-9, in some embodiments, the plunger 304 can include one or more recesses or channels 344. By way of example only, the plunger 304 includes a cap or shroud 346, and in some embodiments, as shown in FIGS. 8-9, each recess 344 can be defined by an outer (circumferential) surface of the plunger 304, a bottom surface the cap 346, and a projection 364. As such, the upper wall 340 of the housing 302, a projection 364, and the plunger cap 346 (e.g., a bottom surface thereof) can be configured such that the upper wall 340 of the housing 102 is positioned at least partially in the recess 344 when the plunger 304 and the housing 302 are rotated relative to one another to slide the projection 364 from a location where it is aligned with a recess 366 to a location under the upper wall 340 (see FIGS. 9 and 9A).

The construction of the twist-lock locking mechanism 336 is shown by way of example only; however, it should be understood that the projections 364 can interact with the housing 302 in a variety of ways besides sliding into place under the upper wall 340 of the housing 302. For example, in some embodiments, the housing 302 can include one or more internal cutouts or slots dimensioned to receive the projections 364 when the plunger 304 and the housing 302 are rotated relative to one another between an unlocked state and a locked state. Still, other suitable twist-lock configurations are also possible and can be employed without departing from the spirit and scope of the present disclosure. During the twist-lock application, the plunger 304 and/or the deformable sheet 310 can be configured (e.g., by being shaped appropriately and/or by being formed of appropriate materials) to allow the plunger 304 to freely rotate with respect to the deformable sheet 310, such that the deformable sheet 310 is not snagged or twisted when the plunger 304 is rotated. Additionally, or alternatively, in some embodiments, an additional layer (e.g., a film or plastic component) can be employed between the plunger 304 and the deformable sheet 310, allowing the plunger 304 to rotate without snagging or twisting the additional layer or the deformable sheet 310. As a result, the microneedles 108 can remain rotationally stationary during the twisting operation.

During use or operation of the applicator 300, a first surface 312 of the housing 302 can be positioned adjacent (or adhered to) the skin of a patient when the plunger 304 and the microneedle device 306 are in their respective first positions $P_1'$, $M_1'$ (see FIG. 8). The plunger 304 can then be depressed downwardly (e.g., along the longitudinal direction $D_L'$), for example, by pressing the plunger 304 via the cap 346 and/or the fins 370. The plunger 304 is moved into the housing 302 (i.e., into the bore 314) to move the plunger 304 and the microneedle device 306 toward their respective second positions $P_2'$, $M_2'$. The plunger 304 can be moved a (vertical) distance toward the skin until a force has been reached that is sufficient to deform the deformable sheet 310 and to move the plunger 304 and the microneedle device 306 from their respective first positions $P_1'$, $M_1'$ toward their respective second positions $P_2'$, $M_2'$ while passing the projections 364 through recesses 366 (see FIG. 8A). After the projections 364 have passed through the recesses 366 and the plunger 304 and the microneedle device 306 have been moved a sufficient (vertical) distance, the plunger 304 and/or the housing 302 can be rotated or twisted relative to the other (e.g., via the fins 370) to an angular position where the projections 364 are no longer aligned with the recesses 366 in the housing 302, such that the projections 364 are positioned under the upper wall 340 of the housing 302 and the plunger 304 and the microneedle device 306 are locked in their respective second positions $P_2'$, $M_2'$ (see FIGS. 9 and 9A). The bias of the deformable sheet 310 toward the first positions $P_1'$, $M_1'$ of the plunger 304 and the microneedle device 306 can facilitate locking the projections 364 against the upper wall 340 of the housing 302. The applicator 300 can then remain in the actuated state with the plunger 304 and the microneedle device 306 locked in their respective second positions $P_2'$, $M_2'$ until a desired treatment and/or delivery period has elapsed. At that time, the entire applicator 300 can be removed from the skin.

Figure 10:
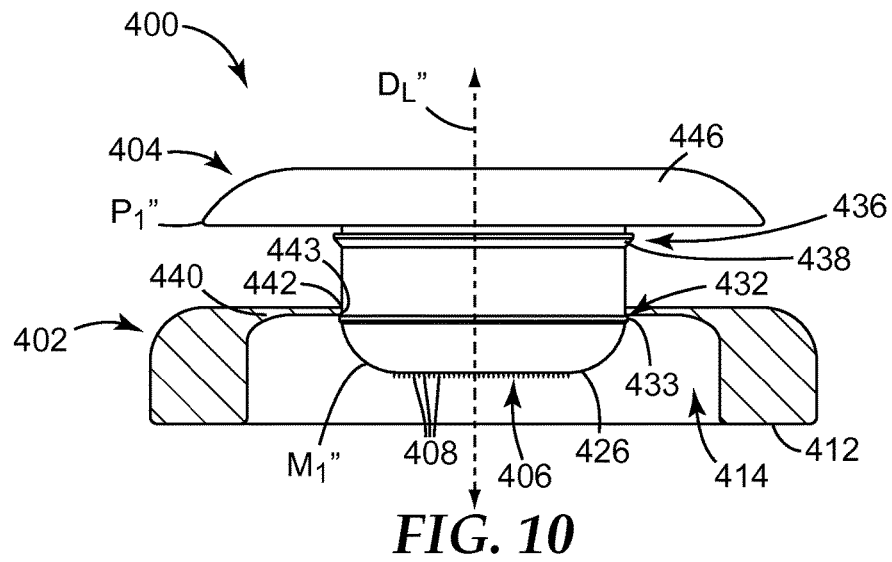
FIG. 10 is a side partial cross-sectional view of an applicator according to another embodiment of the present disclosure, the applicator shown unactuated.
Figure 11:
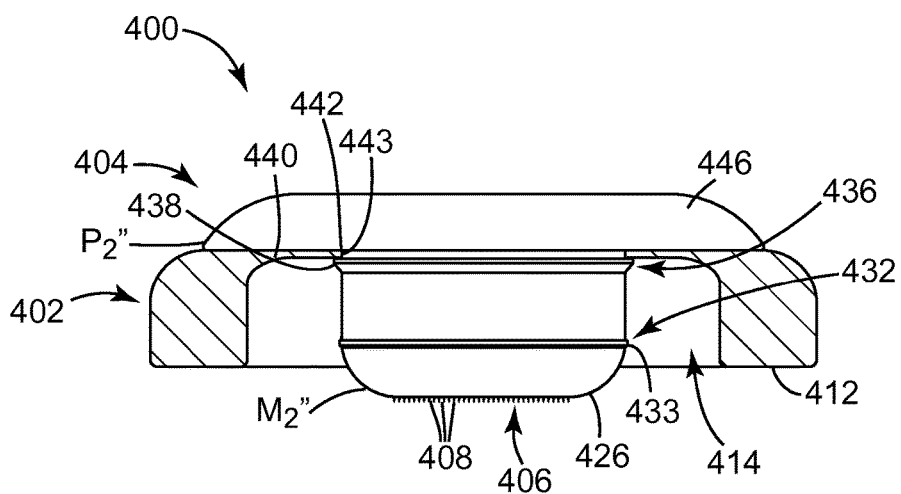
FIG. 11 is a side partial cross-sectional view of an applicator according to another embodiment of the present disclosure, the applicator shown actuated.

FIGS. 10-11 illustrate an applicator 400 according to another embodiment of the present disclosure. The applicator 400 includes a housing 402, a plunger 404, a microneedle device 406 comprising microneedles 408, and a locking mechanism 436. The plunger 404 includes a cap or shroud 446. The applicator 400 is essentially the same as the applicator 100 of FIGS. 1-6, except that the applicator 400 of FIGS. 10-11 does not include a deformable sheet; the microneedle device 406 is coupled to the plunger 404 (e.g., to a first end 426 of the plunger 404); and the housing 402 is formed of a single, unitary body (although this need not be the case).

As shown in FIGS. 10-11, the housing 402 can include an upper (annular) wall 440 that defines an aperture 442 formed therein through which the plunger 404 can move into a bore 414 formed in the housing 402. The plunger 404 includes one or more retaining features 432, including a first (annular) flange or detent 433 configured to interact with the housing 402 (e.g., the upper wall 440 of the housing 402) to inhibit undesired removal of the plunger 404 from the bore 414. The plunger 404 further includes a locking mechanism 436 configured to lock the plunger 404 and the microneedle device 406 in their respective second positions $P_2''$, $M_2''$ (see FIG. 11). The locking mechanism 436 includes a second (annular) flange or detent 438 that interacts with the housing 402 (e.g., the upper wall 440 of the housing 402).

Similar to the locking mechanism 136 of the applicator 100, by way of example only, the locking mechanism 436 includes elements of the plunger 404 and elements of the housing 402, and an interaction or inter-engagement therebetween.

In some embodiments in which no deformable sheet is employed, the interference fit between the housing 402 (e.g., the upper wall 440 of the housing 402) and the plunger 404 (e.g., an outer (circumferential) surface of the plunger 404) can be configured (e.g., can be tighter) to provide a certain amount of resistance and/or stability in moving the plunger 404 and the microneedle device 406 from their first position $P_1''$, $M_1''$ (see FIG. 10) to their second position $P_2''$, $M_2''$. That is, the relative dimensions of the outer surface of the plunger 404 and the aperture 442 formed in the upper wall 440 of the housing 402 can be controlled to achieve a desired interference fit and force necessary to move the plunger 404 relative to the aperture 442 and to engage the locking mechanism 436.

As mentioned above, in some embodiments that do employ a deformable sheet (e.g., the deformable sheet 110 of the embodiment of FIGS. 1-6), the deformable sheet can facilitate applying an active agent to the microneedles of the microneedle device (e.g., prior to packaging, shipment, storage and/or use) because the deformable sheet can provide a bias toward the first position (e.g., $P_1$, $M_1$) of the plunger and the microneedle device. Such a bias can facilitate returning the microneedle device from its application position (e.g., the third position $M_3$ shown in dashed in FIG. 4) to its first position $M_1$ prior to applying the applicator to a patient's skin.

Even though a deformable sheet may facilitate applying an active agent to a microneedle device, the applicator 400 of FIGS. 10-11 can also be configured for applying an active agent to the microneedles 408. For example, in some embodiments, the vertical distance on the plunger 404 between the first flange 433 and the second flange 438 can be controlled to allow the microneedle device 406 to be positioned beyond a first, skin-contacting surface 412 of the housing 402 without engaging the locking mechanism 436. Also, the relative dimensions of the outer surface of the plunger 404 and the aperture 442 can be controlled to allow the plunger 404 to be moved through the aperture 442 with enough ease to facilitate application of an active agent without allowing the locking mechanism 436 to be undesirably engaged.

As mentioned above, the microneedle device 406 and the plunger 404 of the applicator 400 are coupled together, such that the movement of the plunger 404 relative to the housing 402 directly controls the positioning of the microneedle device 406. By way of example only, in the embodiment illustrated in FIGS. 10-11, the microneedle device 406 is integrally formed in a first end 426 of the plunger 404. As such, the applicator 400 does not include an array carrier. However, it should be understood that other constructions are possible. For example, in some embodiments, the microneedle device 406 can be coupled directly to the plunger 404 (e.g., the first end 426 of the plunger 404), or the microneedle device 406 can be indirectly coupled to the plunger 404 via one or more intervening layers, such as an array carrier (similar to the carrier 124 of FIGS. 1-6).

During use or operation of the applicator 400, the first surface 412 of the housing 402 can be positioned adjacent (or adhered to) the skin of a patient when the plunger 404 and the microneedle device 406 are in their respective first positions $P_1''$, $M_1''$. The plunger 404 can then be depressed downwardly (e.g., along a longitudinal direction $D_L''$ (see FIG. 10)) into the housing 402 (i.e., into the bore 414) to move the plunger 404 and the microneedle device 406 toward their respective second positions $P_2''$, $M_2''$. When the plunger 404 has been moved a sufficient (vertical) distance toward the skin and a force has been reached that is sufficient to overcome the interference between the housing 402 (e.g., an inner surface 443 defined by the aperture 442) and the second flange 438 of the plunger 404 (i.e., to engage the locking mechanism 436), the plunger 404 and the microneedle device 406 can be locked in their respective second positions $P_2''$, $M_2''$ (see FIG. 11). The applicator 400 can then remain in the actuated state with the plunger 404 and the microneedle device 406 locked in their respective second positions $P_2''$, $M_2''$ until a desired treatment and/or delivery period has elapsed. At that time, the entire applicator 400 can be removed from the patient's skin.

Each embodiment shown in the figures is illustrated as a separate embodiment for clarity in illustrating a variety of features of the applicators of the present disclosure. However, it should be understood that any combination of elements and features of any of the embodiments illustrated in the figures and described herein can be employed in the applicators of the present disclosure.

The following embodiments are intended to be illustrative of the present disclosure and not limiting.

EMBODIMENTS

Embodiment 1 is an applicator for applying a microneedle device to a skin surface, the applicator comprising:
  a microneedle device;
  a housing configured to house at least a portion of the microneedle device, the housing having a first surface configured to be positioned toward the skin surface;
  an unactuated state in which the microneedle device is located within the housing and does not extend beyond the first surface of the housing;
  an actuated state in which at least a portion of the microneedle device extends beyond the first surface of the housing; and
  a locking mechanism configured to lock the applicator in the actuated state.

Embodiment 2 is a method of applying a microneedle device to a skin surface, the method comprising:
  providing an applicator comprising
    a microneedle device,
    a housing configured to house at least a portion of the microneedle device, the housing having a first surface configured to be positioned toward the skin surface,
    an unactuated state in which the microneedle device is located within the housing and does not extend beyond the first surface of the housing, and
    an actuated state in which at least a portion of the microneedle device extends beyond the first surface of the housing;
  positioning the first surface of the housing of the applicator adjacent the skin surface;
  actuating the applicator to cause the applicator to change to the actuated state; and
  locking the applicator in the actuated state.

Embodiment 3 is a skin treatment device comprising the applicator assembly of embodiment 1.

Embodiment 4 is the applicator of embodiment 1 or the method of embodiment 2, wherein the locking mechanism is configured to reversibly lock the applicator in the actuated state.

Embodiment 5 is the applicator of embodiment 1, further comprising an actuator configured to change the applicator from the unactuated state to the actuated state.

Embodiment 6 is the method of embodiment 2, wherein the applicator further comprises an actuator configured to change the applicator from the unactuated state to the actuated state.

Embodiment 7 is the applicator or the method of embodiment 6, wherein the actuator includes a plunger configured to move between a first position and a second position to move the microneedle device, respectively, between
  a first position in which the microneedle device is located within the housing and recessed relative to the first surface of the housing, and
  a second position in which at least a portion of the microneedle device extends beyond the first surface of the housing.

Embodiment 8 is the applicator of any of embodiments 1, 4, 5 and 7 or the method of any of embodiments 2, 6 and 7, wherein the housing further includes a bore that extends through the first surface, the applicator further comprising:
  a deformable sheet positioned to extend across the bore of the housing, the deformable sheet having a first side oriented toward the first surface of the housing and a second side opposite the first side;
  a microneedle device coupled to the first side of the deformable sheet, and
  a plunger dimensioned to be at least partially received in the bore of the housing adjacent the second side of deformable sheet and located opposite the deformable sheet from the microneedle device, the plunger being movable relative to the housing between a first position and a second position to move the microneedle device, respectively, between
    a first position in which the microneedle device is recessed relative to the first surface of the housing, and
    a second position in which at least a portion of the microneedle device extends beyond the first surface of the housing.

Embodiment 9 is the applicator or method of embodiment 8, wherein the locking mechanism is configured to lock the microneedle device in the second position.

Embodiment 10 is the applicator or method of embodiment 8 or 9, wherein the locking mechanism is activated when the plunger is moved into the second position.

Embodiment 11 is the method of any of embodiments 8-10, wherein locking the applicator in the actuated state includes locking the microneedle device in the second position.

Embodiment 12 is the method of any of embodiments 8-11, wherein locking the applicator in the actuated state includes moving the plunger from the first position to the second position.

Embodiment 13 is the method of any of embodiments 8-12, wherein actuating the applicator to cause the applicator to change to the actuated state includes moving the plunger and the microneedle device from the first position to the second position.

Embodiment 14 is the method of any of embodiments 2, 6, 7 and 8-13, wherein actuating the applicator occurs after positioning the first surface of the housing of the applicator adjacent the skin surface.

Embodiment 15 is an applicator for applying a microneedle device to a skin surface, the applicator comprising:
- a housing having a first surface configured to be positioned toward the skin surface, the housing comprising a bore that that extends through the first surface;
- a microneedle device comprising an array of microneedles oriented toward the first surface of the housing;
- a plunger dimensioned to be at least partially received in the bore of the housing located adjacent the microneedle device, the plunger being movable relative to the housing between a first position and a second position to move the microneedle device, respectively, between
  - a first position in which the microneedle device is recessed relative to the first surface of the housing, and
  - a second position in which at least a portion of the microneedle device extends beyond the first surface of the housing; and
- a locking mechanism configured to lock the microneedle device in the second position.

Embodiment 16 is an applicator for applying a microneedle device to a skin surface, the applicator comprising:
- a housing having a first surface configured to be positioned toward the skin surface, the housing comprising a bore that extends through the first surface;
- a deformable sheet positioned to extend across the bore of the housing, spaced a distance from the first surface of the housing, the deformable sheet having a first side oriented toward the first surface of the housing and a second side opposite the first side;
- a microneedle device coupled to the first side of the deformable sheet, such that the microneedle device is oriented toward the first surface of the housing;
- a plunger dimensioned to be at least partially received in the bore of the housing adjacent the second side of deformable sheet and located opposite the deformable sheet from the microneedle device, the plunger being movable relative to the housing between a first position and a second position to move the microneedle device, respectively, between
  - a first position in which the microneedle device is recessed relative to the first surface of the housing, and
  - a second position in which at least a portion of the microneedle device extends beyond the first surface of the housing; and
- a locking mechanism configured to lock the microneedle device in the second position.

Embodiment 17 is a method of applying a microneedle device to a skin surface, the method comprising:
- providing an applicator comprising
  - a housing having a first surface configured to be positioned toward the skin surface, the housing comprising a bore that that extends through the first surface,
  - a microneedle device comprising a microneedle array of microneedles oriented toward the first surface of the housing, and
  - a plunger dimensioned to be at least partially received in the bore of the housing located adjacent the microneedle array, the plunger being movable relative to the housing between a first position and a second position to move the microneedle device, respectively, between
    - a first position in which the microneedle device is recessed relative to the first surface of the housing, and
    - a second position in which at least a portion of the microneedle device extends beyond the first surface of the housing;
- positioning the first surface of the housing adjacent the skin surface;
- moving the plunger from the first position to the second position to move the microneedle device from the first position to the second position; and
- locking the microneedle device in the second position.

Embodiment 18 is a method of applying a microneedle device to a skin surface, the method comprising:
- providing an applicator comprising
  - a housing having a first surface configured to be positioned toward the skin surface, the housing comprising a bore that extends through the first surface,
  - a deformable sheet positioned to extend across the bore of the housing, the deformable sheet having a first side oriented toward the first surface of the housing and a second side opposite the first side,
  - a microneedle device coupled to the first side of the deformable sheet, such that the microneedle device is oriented toward the first surface of the housing, and
  - a plunger dimensioned to be at least partially received in the bore of the housing adjacent the second side of deformable sheet and located opposite the deformable sheet from the microneedle device, the plunger being movable relative to the housing between a first position and a second position to move the microneedle device, respectively, between
    - a first position in which the microneedle device is recessed relative to the first surface of the housing, and
    - a second position in which at least a portion of the microneedle device extends beyond the first surface of the housing;
- positioning the first surface of the housing adjacent the skin surface;
- moving the plunger from the first position to the second position; and
- locking the microneedle device in the second position.

Embodiment 19 is the applicator of any of embodiments 7, 8, 15 and 16 or the method of any of embodiments 7, 8, 17 and 18, wherein the plunger and the microneedle device are coupled together in the first position and the second position.

Embodiment 20 is the applicator of embodiment 7 or 15 or the method of embodiment 7 or 17, wherein the plunger and the microneedle device are integrally formed.

Embodiment 21 is the applicator of any of embodiments 8, 16 and 19 or the method of any of embodiments 8, 18 and 19, wherein the housing comprises a first portion and a second portion that each define a portion of the bore, and wherein the deformable sheet is coupled between the first portion and the second portion to extend across the bore.

Embodiment 22 is the applicator or method of embodiment 21, wherein the bore includes a first portion defined by the first portion of the housing and a second portion defined by the second portion of the housing, wherein the plunger resides in the first portion of the bore when the plunger is in the first position, and wherein at least a portion of the plunger resides in the second portion of the bore when the plunger is in the second position.

Embodiment 23 is the applicator or method of embodiment 22, wherein the microneedle device resides in the second portion of the bore when the plunger is in the first position.

Embodiment 24 is the applicator of any of embodiments 7, 8, 15, 16 and 19-23 or the method of any of embodiments 7, 8 and 17-23, wherein the plunger is moved between the first position and the second position with manual pressure.

Embodiment 25 is the applicator of any of embodiments 7, 8, 15, 16 and 19-24 or the method of any of embodiments 7, 8 and 17-24, wherein at least a portion of the microneedle device is pushed into the skin surface when the plunger is in the second position.

Embodiment 26 is the applicator of any of embodiments 7, 8, 15, 16 and 19-25 or the method of any of embodiments 7, 8 and 17-25, wherein the plunger is further movable to a third position located intermediately of the first position and the second position.

Embodiment 27 is the applicator of any of embodiments 7, 8, 15, 16 and 19-26 or the method of any of embodiments 7, 8 and 17-26, wherein:
the first position of the plunger is a first unlocked position in which the locking mechanism is not activated,
the second position of the plunger is a second locked position in which the locking mechanism is activated when the plunger is moved into the second locked position, and
the plunger is further movable to a third unlocked position located intermediately of the first position and the second position in which at least a portion of the microneedle device extends beyond the first surface of the housing but in which the locking mechanism is not activated.

Embodiment 28 is the applicator or method of embodiment 27, wherein the locking mechanism is activated when a threshold force has been overcome, and wherein the force necessary to move the plunger to the third unlocked position is not sufficient to exceed the threshold force and activate the locking mechanism.

Embodiment 29 is the applicator or method of embodiment 28, wherein the force necessary to move the plunger to the second locked position is sufficient to activate the locking mechanism.

Embodiment 30 is the applicator or method of any of embodiments 7, 8, 15, 16 and 19-29 or the method of any of embodiments 7, 8 and 17-29, wherein the locking mechanism is activated when the plunger is moved into the second position.

Embodiment 31 is the applicator or method of any of embodiments 8, 16 and 19-30 or the method of any of embodiments 8 and 18-30, wherein the deformable sheet and the housing define a recess within which the microneedle device resides when the plunger is in the first position.

Embodiment 32 is the applicator or method of embodiment 31, wherein the housing is formed of a first portion and a second portion that each define a portion of the bore, wherein the deformable sheet is coupled between the first portion and the second portion to extend across the bore, and wherein the recess is defined by the deformable sheet and the second portion of the housing.

Embodiment 33 is the applicator or method of any of embodiments 8, 16 and 19-32 or the method of any of embodiments 8 and 18-32, wherein the deformable sheet has a first state and a second state, wherein the deformable sheet is in the first state when the plunger is in the first position, and wherein the deformable sheet is in the second state when the plunger is in the second position.

Embodiment 34 is the applicator or method of embodiment 33, wherein the microneedle device is located within the housing and recessed relative to the first surface of the housing when the deformable sheet is in the first state.

Embodiment 35 is the applicator or method of any of embodiments 8, 16 and 19-34 or the method of any of embodiments 8 and 18-34, wherein the deformable sheet is formed of a nonwoven polyurethane.

Embodiment 36 is the method of any of embodiments 17-35, wherein the plunger is further movable to a third position where the microneedle device is located at a third position located intermediately of its first position and the second position, and further comprising:
moving the plunger to the third position to move the microneedle device to its third position;
coating at least a portion of the microneedle device with an active agent when the microneedle device is in the third position; and
moving the plunger and the microneedle device from the third position to a position at which the coated microneedle device is located within the housing.

Embodiment 37 is a method for coating a microneedle device with an active agent, the method comprising:
providing an applicator comprising
a housing having a first surface configured to be positioned toward the skin surface, the housing comprising a bore that extends through the first surface,
a deformable sheet positioned to extend across the bore of the housing, the deformable sheet having a first side oriented toward the first surface of the housing and a second side opposite the first side,
a microneedle device coupled to the first side of the deformable sheet, such that the microneedle device is oriented toward the first surface of the housing,
a plunger dimensioned to be at least partially received in the bore of the housing adjacent the second side of deformable sheet and located opposite the deformable sheet from the microneedle device, the plunger being movable relative to the housing between a first position, a second position and a third position to move the microneedle device, respectively between
a first position in which the microneedle device is recessed relative to the first surface of the housing,
a second position in which the microneedle device extends beyond the first surface of the housing and a locking mechanism is activated to lock the plunger and the microneedle device in the second position, and
a third position located intermediately of the first position and the second position in which at least a portion of the microneedle device extends beyond the first surface of the housing;
coating at least a portion of the microneedle device with the active agent by moving the plunger and the microneedle device to the third position; and
moving the plunger and the microneedle device from the third position to a position at which the coated microneedle device is located within the housing.

Embodiment 38 is the method of embodiment 36 or 37, further comprising:
positioning the first surface of the housing adjacent the skin surface;

moving the plunger from the first position to the second position to press at least a portion of the coated microneedle device into the skin surface; and locking the microneedle device in the second position.

Embodiment 39 is an applicator for applying a microneedle device to a skin surface, the applicator comprising:

a housing having a first surface configured to be positioned toward the skin surface, the housing comprising a bore that extends through the first surface;

a deformable sheet positioned to extend across the bore of the housing such that the deformable sheet is spaced a distance from the first surface of the housing, the deformable sheet having a first side oriented toward the first surface of the housing and a second side opposite the first side, the deformable sheet having a first state and a second state;

a microneedle device coupled to the first side of the deformable sheet, such that the microneedle device is oriented toward the first surface of the housing and is located within the housing and recessed relative to the first surface of the housing when the deformable sheet is in the first state;

a plunger dimensioned to be at least partially received in the bore of the housing adjacent the second side of the deformable sheet and located opposite the deformable sheet from the microneedle device, the plunger being movable relative to the housing between a first position and a second position to move the microneedle device, respectively, between a first position in which the deformable sheet is in its first state, and in which the microneedle device is located within the bore of the housing and recessed relative to the first surface of the housing, and a second position in which the deformable sheet is in its second state and at least a portion of the microneedle device extends beyond the first surface of the housing; and a locking mechanism configured to lock the microneedle device in the second position.

Embodiment 40 is the applicator of any of embodiments 1, 4, 5, 7-10, 15-16, 19-35 and 39 or the method of any of embodiments 2, 6, 7-14 and 17-39, wherein the locking mechanism changes from an unactivated state to an activated state when a threshold force has been overcome.

Embodiment 41 is the applicator of any of embodiments 1, 4, 5, 7-10, 15-16, 19-35, and 39-40 or the method of any of embodiments 2, 6, 7-14 and 17-40, wherein the locking mechanism includes at least one of a snap-fit-type engagement, a detent, a twist lock, or a combination thereof.

Embodiment 42 is the applicator of any of embodiments 1, 4, 5, 7-10, 15-16, 19-35, and 39-41 or the method of any of embodiments 2, 6, 7-14 and 17-41, wherein the locking mechanism is irreversible.

Embodiment 43 is the applicator of any of embodiments 1, 4, 5, 7-10, 15-16, 19-35, and 39-42 or the method of any of embodiments 2, 6, 7-14 and 17-42, wherein the first surface of the housing includes a skin-contact adhesive.

Embodiment 44 is the applicator of any of embodiments 1, 4, 5, 7-10, 15-16, 19-35, and 38-43 or the method of any of embodiments 2, 6, 7-14 and 17-43, wherein the microneedle device includes solid microneedles.

The following working example is intended to be illustrative of the present disclosure and not limiting.

EXAMPLE

An applicator of the design shown in FIGS. 1-6 and described above was used in the example. The plunger and housing components of the applicator were fabricated from white Delrin® acetal resin (DuPont Corporation, Wilmington, Del.) using a machining process. The external housing dimensions were about 37.4 mm (diameter) by about 6.5 mm (overall height). The aperture in an upper wall of the housing for the plunger was about 15.9 mm in diameter. The upper wall of the first upper portion of the housing around the aperture was about 0.40 mm thick.

The plunger was fabricated as a single piece. The first (lower) flange and the second (upper) flange on the plunger were separated by a distance of about 3.98 mm (as measured from the bottom surface of one flange to the bottom surface of the other flange). The outer diameter of each flange measured about 16.1 mm. The second flange located at the upper portion of the plunger was about 0.79 mm thick with an about 0.13 mm by 45 degree chamfer at its bottom edge (the bottom edge of the flange faced the base of the second (lower) portion of the housing). The first flange located at the lower portion of the plunger was about 0.41 mm thick with an about 0.13 mm by 45 degree chamfer at its bottom edge. After actuation, the final resting (locked) position of the base of the microneedle array (i.e., from which the microneedles extend) extended beyond the base (or first surface) of the lower housing by a distance of about 2.16 mm.

The deformable sheet was about 37.4 mm in diameter and was constructed from CoTran 9700 (3M Company, St. Paul, Minn.), a melt-blown polyurethane nonwoven having a nominal thickness of 0.23 mm. The deformable sheet was attached to both the first and second portions of the housing (i.e., sandwiched therebetween) using a continuous coating of 3M Double Coated Medical Tape 1513 (3M Company, St. Paul, Minn.). The microneedle array was also attached to the deformable sheet using 3M Double Coated Medical Tape 1513 (3M Company, St. Paul, Minn.).

Microneedle Depth of Penetration Study

A study was conducted to determine the depth of penetration (DOP) of the microneedles of the array when applied to the skin surface of Yorkshire cross domestic pigs (Midwest Research Swine, Gibbon, Minn.), in vivo. Each array was molded into a 1.3 cm² square using Vectra MT1300 liquid crystal polymer (LCP) (Ticona Engineering Polymers, Florence, Ky.) and featured four-sided pyramidal-shaped microneedles in a pattern of 15 rows×15 columns. Each microneedle had a height of about 680 microns with an aspect ratio of 3:1. The spacing between individual microneedles was about 500 microns (as measured from tip to tip).

The microneedles were coated using a three step process. The first two steps involved applying primer coatings to the microneedles and the third step involved applying a thin coating of Rhodamine B to the microneedles. In Step 1, the arrays were flood coated with a 35 µl solution containing 0.5 mg/mL polyvinyl alcohol (80% hydrolyzed) (Sigma-Aldrich, Inc., St. Louis, Mo.) and 35 µg/ml of TWEEN® 80 (Sigma-Aldrich) in 90% (w/v) ethanol. The coated arrays were then dried at 35° C. for 20 minutes. In Step 2, the arrays from Step 1 were flood coated with 35 µl of an aqueous solution of 33.3 mg/ml Alum Potassium Sulfate (Penta Manufacturing, Livingston, N.J.). The coated arrays were then dried at 35° C. for 30 minutes. In Step 3, the primed arrays from Step 2 were flood coated with 40 µl of an aqueous solution of 0.08% (w/v) Rhodamine B (Sigma-Aldrich). The coated arrays were dried at 35° C. for 30 minutes. The three step process provided arrays in which the microneedles were completely covered with a thin, opaque coating of Rhodamine B.

Application sites on the animals were shaved. The animals were anesthetized with isoflurane gas and maintained under anesthesia throughout the experiment.

The fully assembled applicators were applied to the pig skin with double-sided pressure-sensitive tape. The shaft of a CHATILLON® model DFS-050 force gauge (AMTEK, Inc., Largo, Fla.) was used to provide application force to the plunger of the applicator. Once the applicator was locked-in-place (i.e., with the plunger and the microneedle device in their second, locked, positions, with the locking mechanism engaged), the applied force was removed and the applicator was maintained on the skin for an additional 15 minutes. Arrays (n=4) were applied to both the upper and lower ham areas.

The applicator was removed from the animal. The depth of penetration (DOP) of the microneedles into the pig skin was determined indirectly by measuring the distance from the tip of the microneedle to where the Rhodamine B coating was wiped or dissolved from the microneedle after application into the skin. The measurement was conducted using a Nikon LV-100 microscope at 100× magnification (Nikon Instruments, Melville, N.Y.) with Image Pro® Plus digital image analysis software (Media Cybernetics, Bethesda, Md.). The mean DOP was determined by sampling a subset of 66 microneedles from each array. Each array pattern was divided into four quadrants and relatively equal numbers of microneedles were sampled from each quadrant. The results are presented in Tables 1 and 2.

TABLE 1

DOP for Application to the Lower Ham Area

| Application Force | 67-89 N |
| --- | --- |
| Mean DOP (n = 4) | 106 microns |
| Standard Deviation | 27 microns |
| % RSD | 25 |

TABLE 2

DOP for Application to the Upper Ham Area

| Application Force | 62-80 N |
| --- | --- |
| Mean DOP (n = 4) | 149 microns |
| Standard Deviation | 21 microns |
| % RSD | 14 |

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. An applicator for applying a microneedle device to a skin surface, the applicator comprising:
    a housing having a first surface configured to be positioned toward the skin surface, the housing comprising a bore that extends through the first surface;
    a deformable sheet positioned to extend across the bore of the housing, spaced a distance from the first surface of the housing, the deformable sheet having a first side oriented toward the first surface of the housing and a second side opposite the first side;
    a microneedle device coupled to the first side of the deformable sheet, such that the microneedle device is oriented toward the first surface of the housing;
    a plunger dimensioned to be at least partially received in the bore of the housing adjacent the second side of the deformable sheet and located opposite the deformable sheet from the microneedle device, the plunger being movable relative to the housing between a first position and a second position to move the microneedle device, respectively, between
        a first position of the plunger in which the microneedle device is recessed relative to the first surface of the housing, and
        a second position of the plunger in which at least a portion of the microneedle device extends beyond the first surface of the housing and towards the skin surface; and
    a locking mechanism configured to lock the microneedle device in the second position, wherein:
    the first position of the plunger is a first unlocked position in which the locking mechanism is not activated,
    the second position of the plunger is a second locked position in which the locking mechanism is activated when the plunger is moved into the second locked position, and
    the plunger is further movable to a third unlocked position of the plunger located intermediately of the first position of the plunger and the second position of the plunger in which at least a portion of the microneedle device extends beyond the first surface of the housing but in which the locking mechanism is not activated.

2. The applicator of claim 1, wherein the plunger and the microneedle device are coupled together when the plunger is in the first position of the plunger and the microneedle device is in the second position, and are also coupled together when the plunger is in the second position of the plunger and the microneedle device is in the second position.

3. The applicator of claim 1, wherein the housing comprises a first portion and a second portion that each define a portion of the bore, and wherein the deformable sheet is coupled between the first portion and the second portion to extend across the bore.

4. The applicator of claim 3, wherein the bore includes a first portion defined by the first portion of the housing and a second portion defined by the second portion of the housing, wherein the plunger resides in the first portion of the bore when the plunger is in the first position, and wherein at least a portion of the plunger resides in the second portion of the bore when the plunger is in the second position.

5. The applicator of claim 1, wherein the plunger is configured to be moved between the first position of the plunger and the second position of the plunger with manual pressure.

6. The applicator of claim 1, wherein the locking mechanism is activated when a threshold force has been overcome, and wherein a force necessary to move the plunger to the third unlocked position is not sufficient to exceed the threshold force and activate the locking mechanism.

7. The applicator of claim 6, wherein a force necessary to move the plunger to the second locked position is sufficient to activate the locking mechanism.

8. The applicator of claim 1, wherein the locking mechanism is activated when the plunger is moved into the second position.

9. The applicator of claim 1, wherein the deformable sheet has a first state and a second state, wherein the deformable sheet is in the first state when the plunger is in the first position of the plunger, and wherein the deformable sheet is in the second state when the plunger is in the second position of the plunger.

10. The applicator of claim 1, wherein the deformable sheet is formed of a nonwoven polyurethane.

11. The applicator of claim 1, wherein the locking mechanism is configured to reversibly lock the applicator in an actuated state.

12. The applicator of claim 1, wherein the locking mechanism includes at least one of a snap-fit-type engagement, a detent, a twist lock, or a combination thereof.

13. The applicator of claim 1, wherein the microneedle device includes solid microneedles.

14. The applicator of claim 1, wherein the locking mechanism is irreversible.

15. The applicator of claim 1, wherein the first surface of the housing includes a skin-contact adhesive.

16. An applicator for applying a microneedle device to a skin surface, the applicator comprising:
   a housing having a first surface configured to be positioned toward the skin surface, the housing comprising a bore that extends through the first surface;
   a deformable sheet positioned to extend across the bore of the housing, spaced a distance from the first surface of the housing, the deformable sheet having a first side oriented toward the first surface of the housing and a second side opposite the first side;
   a microneedle device coupled to the first side of the deformable sheet, such that the microneedle device is oriented toward the first surface of the housing;
   a plunger dimensioned to be at least partially received in the bore of the housing adjacent the second side of the deformable sheet and located opposite the deformable sheet from the microneedle device, the plunger being movable relative to the housing between a first position and a second position to move the microneedle device, respectively, between
      a first position of the plunger in which the microneedle device is recessed relative to the first surface of the housing, and
      a second position of the plunger in which at least a portion of the microneedle device extends beyond the first surface of the housing and towards the skin surface; and
   a locking mechanism configured to lock the microneedle device in the second position,
   wherein the deformable sheet is formed of a nonwoven polyurethane.

17. The applicator of claim 16, wherein the plunger and the microneedle device are coupled together when the plunger is in the first position of the plunger and the microneedle device is in the second position, and are also coupled together when the plunger is in the second position of the plunger and the microneedle device is in the second position.

18. The applicator of claim 16, wherein the housing comprises a first portion and a second portion that each define a portion of the bore, and wherein the deformable sheet is coupled between the first portion and the second portion to extend across the bore.

19. The applicator of claim 16, wherein the locking mechanism is activated when the plunger is moved into the second position.

* * * * *

UNITED STATES PATENT AND TRADEMARK OFFICE
CERTIFICATE OF CORRECTION

| | | |
|---|---|---|
| PATENT NO. | : 10,300,260 B2 | Page 1 of 1 |
| APPLICATION NO. | : 14/432500 | |
| DATED | : May 28, 2019 | |
| INVENTOR(S) | : David Wirtanen | |

It is certified that error appears in the above-identified patent and that said Letters Patent is hereby corrected as shown below:

In the Specification

Column 2
Line 55, Delete "that that" and insert -- that --, therefor.

Column 3
Line 33, Delete "that that" and insert -- that --, therefor.

Column 6
Line 38, Delete "expired" and insert -- expired. --, therefor.

Column 12
Line 40, Delete "parallelipipedal" and insert -- parallelepipedal --, therefor.

Column 19
Line 31, Delete "exanatide);" and insert -- exenatide); --, therefor.
Line 39, Delete "metaclopromide," and insert -- metoclopramide, --, therefor.

Column 20
Line 3, Delete "lutenizing" and insert -- luteinizing --, therefor.
Line 47, Delete "pamedronate;" and insert -- pamidronate; --, therefor.

Column 35
Line 10, Delete "that that" and insert -- that --, therefor.
Line 63, Delete "that that" and insert -- that --, therefor.

In the Claims

Column 42
Line 38, In Claim 2, delete "second" and insert -- first --, therefor.

Signed and Sealed this
Twelfth Day of May, 2020

Andrei Iancu
*Director of the United States Patent and Trademark Office*